(12) United States Patent
Manning et al.

(10) Patent No.: US 11,027,027 B2
(45) Date of Patent: Jun. 8, 2021

(54) PYRIDAZINOINDOLE COMPOUNDS AND METHODS FOR PET IMAGING

(71) Applicant: Vanderbilt University, Nashville, TN (US)

(72) Inventors: H. Charles Manning, Nashville, TN (US); Yiu-Yin Cheung, Franklin, TN (US); Jason R. Buck, Nashville, TN (US); Jun Li, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 578 days.

(21) Appl. No.: 15/012,795

(22) Filed: Feb. 1, 2016

(65) Prior Publication Data

US 2016/0220704 A1 Aug. 4, 2016

Related U.S. Application Data

(60) Provisional application No. 62/110,407, filed on Jan. 30, 2015.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *C07D 519/00* | (2006.01) |
| *C07D 487/04* | (2006.01) |
| *C07H 17/04* | (2006.01) |
| *A61K 51/04* | (2006.01) |

(52) U.S. Cl.
CPC ...... *A61K 49/0052* (2013.01); *A61K 49/0041* (2013.01); *A61K 51/0459* (2013.01); *C07D 487/04* (2013.01); *C07D 519/00* (2013.01); *C07H 17/04* (2013.01); *A61K 49/0032* (2013.01)

(58) Field of Classification Search
None
See application file for complete search history.

(56) References Cited

U.S. PATENT DOCUMENTS

| | | | |
|---|---|---|---|
| 7,338,651 B2 | 3/2008 | Manning et al. | |
| 7,754,884 B2 | 7/2010 | Manning et al. | |
| 8,188,116 B2 | 5/2012 | Manning et al. | |
| 8,323,621 B2 | 12/2012 | Manning et al. | |
| 8,372,868 B2 | 2/2013 | Manning et al. | |
| 8,841,320 B2 | 9/2014 | Manning et al. | |
| 2015/0044141 A1* | 2/2015 | Pomper ................ | C07D 487/04 424/9.6 |

FOREIGN PATENT DOCUMENTS

WO 2016040527 3/2016

OTHER PUBLICATIONS

Dhermain, F. G.; Hau, P.; Lanfermann, H.; Jacobs, A. H.; van den Bent, M. J. Lancet Neurol 2010, 9, 906.
Rheims, S.; Rubi, S.; Bouvard, S.; Bernard, E.; Streichenberger, N.; Guenot, M.; Le Bars, D.; Hammers, A.; Ryvlin, P. Neuro-oncology 2014.
Jansen, N. L.; Suchorska, B.; Wenter, V.; Eigenbrod, S.; Schmid-Tannwald, C.; Zwergal, A.; Niyazi, M.; Drexler, M.; Bartenstein, P.; Schnell, O.; Tonn, J. C.; Thon, N.; Kreth, F. W.; la Fougere, C. Journal of nuclear medicine : official publication, Society of Nuclear Medicine 2014, 55, 198.
Schwarzenberg, J.; Czernin, J.; Cloughesy, T. F.; Ellingson, B. M.; Pope, W. B.; Grogan, T.; Elashoff, D.; Geist, C.; Silverman, D. H.; Phelps, M. E.; Chen, W. Clinical cancer research : an official journal of the American Association for Cancer Research 2014, 20, 3550.
Goldman, S.; Pirotte, B. J. Methods Mol Biol 2011, 727, 291.
La Fougere, C.; Suchorska, B.; Bartenstein, P.; Kreth, F. W.; Tonn, J. C. Neuro Oncol 2011, 13, 806.
Pirotte, B.; Goldman, S.; Massager, N.; David, P.; Wikler, D.; Vandesteene, A.; Salmon, I.; Brotchi, J.; Levivier, M. Journal of nuclear medicine : official publication, Society of Nuclear Medicine 2004, 45, 1293.
Deane, N. G.; Manning, H. C.; Foutch, A. C.; Washington, M. K.; Aronow, B. J.; Bornhop, D. J.; Coffey, R. J. Mol Cancer Res 2007, 5, 341.
Wyatt, S. K.; Manning, H. C.; Bai, M.; Bailey, S. N.; Gallant, P.; Ma, G.; McIntosh, L.; Bornhop, D. J. Mol Imaging Biol 2010, 12, 349.
Manning, H. C.; Goebel, T.; Thompson, R. C.; Price, R. R.; Lee, H.; Bornhop, D. J. Bioconjug Chem 2004, 15, 1488.
Buck, J. R.; McKinley, E. T.; Hight, M. R.; Fu, A.; Tang, D.; Smith, R. A.; Tantawy, M. N.; Peterson, T. E.; Colvin, D.; Ansari, M. S.; Baldwin, R. M.; Zhao, P.; Guleryuz, S.; Manning, H. C. Journal of nuclear medicine : official publication, Society of Nuclear Medicine 2011, 52, 107.
Tang, D.; Hight, M. R.; McKinley, E. T.; Fu, A.; Buck, J. R.; Smith, R. A.; Tantawy, M. N.; Peterson, T. E.; Colvin, D. C.; Ansari, M. S.; Nickels, M.; Manning, H. C. Journal of nuclear medicine : official publication, Society of Nuclear Medicine 2012, 53, 287.
Tang, D.; McKinley, E. T.; Hight, M. R.; Uddin, M. I.; Harp, J. M.; Fu, A.; Nickels, M. L.; Buck, J. R.; Manning, H. C. Journal of medicinal chemistry 2013, 56, 3429.
Papadopoulos, V.; Baraldi, M.; Guilarte, T. R.; Knudsen, T. B.; Lacapere, J. J.; Lindemann, P.; Norenberg, M. D.; Nutt, D.; Weizman, A.; Zhang, M. R.; Gavish, M. Trends Pharmacol Sci 2006, 27, 402.
Varrone, A.; Mattsson, P.; Forsberg, A.; Takano, A.; Nag, S.; Gulyas, B.; Borg, J.; Boellaard, R.; Al-Tawil, N.; Eriksdotter, M.; Zimmermann, T.; Schultze-Mosgau, M.; Thiele, A.; Hoffmann, A.; Lammertsma, A. A.; Halldin, C. Eur J Nucl Med Mol Imaging 2013, 40, 921.
Suridjan, I.; Rusjan, P. M.; Voineskos, A. N.; Selvanathan, T.; Setiawan, E.; Strafella, A. P.; Wilson, A. A.; Meyer, J. H.; Houle, S.; Mizrahi, R. Neuroimage 2013.
Takano, A.; Piehl, F.; Hillert, J.; Varrone, A.; Nag, S.; Gulyas, B.; Stenkrona, P.; Villemagne, V. L.; Rowe, C. C.; Macdonell, R.; Tawil, N. A.; Kucinski, T.; Zimmermann, T.; Schultze-Mosgau, M.; Thiele, A.; Hoffmann, A.; Halldin, C. EJNMMI research 2013, 3, 30.
Batarseh, A.; Papadopoulos, V. Mol Cell Endocrinol 2010.

(Continued)

*Primary Examiner* — Michael G. Hartley
*Assistant Examiner* — Melissa J Perreira
(74) *Attorney, Agent, or Firm* — Stites & Harbison PLLC; Richard S. Myers, Jr.

(57) ABSTRACT

Embodiments of the invention include a novel synthesis of the translocator protein (TSPO) ligands, and methods of imaging a molecular events. Also disclosed are compounds for treatment of diseases, including cancer.

7 Claims, 2 Drawing Sheets

(56) References Cited

OTHER PUBLICATIONS

Buck, J. R.; Saleh, S.; Uddin, M. I.; Manning, H. C. Tetrahedron letters 2012, 53, 4161.
Powell, A. E.; Vlacich, G.; Zhao, Z. Y.; McKinley, E. T.; Washington, M. K.; Manning, H. C.; Coffey, R. J. American journal of physiology. Gastrointestinal and liver physiology 2014, 307, G16.
Tang, D.; Nickels, M. L.; Tantawy, M. N.; Buck, J. R.; Manning, H. C. Mol Imaging Biol 2014.
Bribes, E.; Bourrie, B.; Esclangon, M.; Galiegue, S.; Vidal, H.; Casellas, P. Eur J Pharmacol 2002, 452, 111.
Ferzaz, B.; Brault, E; Bourliaud, G.; Robert, J. P.; Poughon, G.; Claustre, Y.; Marguet, F.; Liere, P.; Schumacher, M.; Nowicki, J. P.; Fournier, J.; Marabout, B.; Sevrin, M.; George, P.; Soubrie, P.; Benavides, J.; Scatton, B. J Pharmacol Exp Ther 2002, 301, 1067.
Leducq, N.; Bono, F.; Sulpice, T.; Vin, V.; Janiak, P.; Fur, G. L.; O'Connor, S. E.; Herbert, J. M. J Pharmacol Exp Ther 2003, 306, 828.
Vin, V.; Leducq, N.; Bono, F.; Herbert, J. M. Biochemical and biophysical research communications 2003, 310, 785.
Kunduzova, O. R.; Escourrou, G.; De La Farge, F.; Salvayre, R.; Seguelas, M. H.; Leducq, N.; Bono, F.; Herbert, J. M.; Parini, A. Journal of the American Society of Nephrology : JASN 2004, 15, 2152.
Galiegue, S.; Tinel, N.; Casellas, P. Curr Med Chem 2003, 10, 1563.
Bribes, E.; Galiegue, S.; Bourrie, B.; Casellas, P. Immunology Letters 2003, 85, 13.
Bribes, E.; Bourrie, B.; Casellas, P. Immunology Letters 2003, 88, 241.
Leducq-Alet, N.; Vin, V.; Savi, P.; Bono, F. Biochemical and biophysical research communications 2010, 399, 475.
Scarf, A. M.; Kassiou, M. Journal of nuclear medicine : official publication, Society of Nuclear Medicine 2011, 52, 677.
Owen, D. R.; Yeo, A. J.; Gunn, R. N.; Song, K.; Wadsworth, G.; Lewis, A.; Rhodes, C.; Pulford, D. J.; Bennacef, I.; Parker, C. A.; StJean, P. L.; Cardon, L. R.; Mooser, V. E.; Matthews, P. M.; Rabiner, E. A.; Rubio, J. P. Journal of cerebral blood flow and metabolism : official journal of the International Society of Cerebral Blood Flow and Metabolism 2012, 32, 1.
Yoder, K. K.; Nho, K.; Risacher, S. L.; Kim, S.; Shen, L.; Saykin, A. J. Journal of nuclear medicine : official publication, Society of Nuclear Medicine 2013, 54, 1320.
Thominiaux, C.; Damont, A.; Kuhnast, B.; Demphel, S.; Helleix, S. L.; Boisnard, S.; Rivron, L.; Chauveau, F.; Boutin, H.; Camp, N. V.; Boisgard, R.; Roy, S.; Allen, J.; Rooney, T.; Benavides, J.; Hantraye, P.; Tavitian, B.; Dolle, F. Journal of Labelled Compounds & Radiopharmaceuticals 2010, 53, 767.
Chauveau, F.; Boutin, H.; Van Camp, N.; Thominiaux, C.; Hantraye, P.; Rivron, L.; Marguet, F.; Castel, M. N.; Rooney, T.; Benavides, J.; Dolle, F.; Tavitian, B. Eur J Nucl Med Mol Imaging 2011, 38, 509.
Starostarubinstein, S.; Ciliax, B. J.; Penney, J. B.; Mckeever, P.; Young, A. B. Proceedings of the National Academy of Sciences of the United States of America 1987, 84, 891.
Li, et al., Optimized Translocator Protein Ligand for Optical Molecular Imaging and Screening, Bioconjugate Chem. 2017, 28, 1016-1023.

\* cited by examiner

PYRIDAZINOINDOLE COMPOUNDS AND METHODS FOR PET IMAGING

PRIORITY INFORMATION

This application claims benefit to U.S. Patent Application No. 62/110,407, filed Jan. 30, 2015, the contents of which are incorporated herein by reference.

GOVERNMENT FUNDING

This invention was made with government support under grant numbers CA127349, CA128323, RR17858, CA126588, CA163806, CA095103, and DK058404 awarded by the National Institutes of Health. The government has certain rights in the invention.

FIELD OF THE INVENTION

This invention relates generally to the field of molecular imaging, and more specifically to the field of functional imaging, including translocator protein (TSPO) expression imaging probes that incorporate near-infrared fluorophores as signaling agents.

Additionally, this invention relates generally to the field of targeted drug delivery, including in the areas of cancer treatment.

BACKGROUND OF THE INVENTION

There exists a continuing demand for the development and validation of improved imaging biomarkers for cancer. Such biomarkers may aid in cancer diagnosis, predict clinical outcome, and quantify response to therapeutic intervention. Imaging biomarkers of glioma are limited and routinely include magnetic resonance imaging (MM), computed tomography (CT), and less frequently, positron emission tomography (PET). Of these, PET may be the most suitable given its sensitivity, quantitative nature, and ability to analyze the molecular basis of the tumor. For most oncology studies, 2-deoxy-2-[$^{18}$F]fluoroglucose ([$^{18}$F]FDG) is commonly utilized, as this tracer reflects glucose metabolism, which is usually elevated in cancer cells.

However, relatively high glucose uptake in normal brain results in poor tumor-to-background ratios that can confound glioma detection. Moreover, [$^{18}$F]FDG uptake can be affected by a myriad of tangential metabolic processes. This has created a long felt need to evaluate other PET tracers of metabolism in this setting, including amino acid-based PET probes such as [$^{11}$C]MET,[2] [$^{18}$F]FET,[3] and [$^{18}$F]FDOPA. Unfortunately, while these probes can accumulate in tissues that exhibit enhanced amino acid transport, they can be hampered by nonspecific accumulation. Thus, there remains a need to develop and validate additional PET imaging biomarkers suitable for glioma detection and characterization.

The present inventors have previously explored translocator protein (TSPO) expression as a target for molecular imaging of cancer with PET. TSPO, formerly the peripheral benzodiazepine receptor (PBR), is an 18 kDa protein that takes part in a wide breadth of cellular processes, including cell proliferation, apoptosis, steroid biosynthesis, and cholesterol metabolism. Though TSPO has historically been leveraged as a PET biomarker in neuroinflammation, its elevated expression has also been reported in many types of cancer. This overexpression in tumors has been reported to correlate with disease progression and diminished survival and can be indicative of aggressive and potentially metastatic tumors. Within this context, the present inventors have investigated the use of TSPO PET ligands to image colon cancer, breast cancer, and glioma, as these agents would expectedly serve as useful cancer imaging biomarkers. Moreover, on a mechanistic level, the present inventors have utilized TSPO molecular imaging probes to visualize colon cancers arising in genetically engineered mice with aberrant Tgf-β signaling, as well as tumors arising in mice following loss of Apc function. These studies show the importance TSPO PET agents in detecting key molecular events in oncology and to serve as companion diagnostics alongside targeted inhibitors of these pathways.

BRIEF DESCRIPTION OF THE FIGURES

(FIG. 1A) T$_2$-weighted MRI (coronal). (FIG. 1B) Fused MM-PET (coronal). (FIG. 1C) Dynamic PET (coronal). (FIG. 1D) Dynamic PET (axial). (FIG. 1E) H&E histology. (FIG. 1F) TSPO immunohistochemistry. (FIG. 1G) Typical dynamic PET TAC. (FIG. 1H) Displacement study PET TAC.

(FIG. 2A, FIG. 2D) fluorescent images of 29; (FIG. 2B, FIG. 2E) fluorescent images of Mito Tracker Red; (FIG. 2C, FIG. 2F) merged images of C8 and Mito Tracker Red. (FIG. 2D, FIG. 2E, FIG. 2F) fluorescent images of the chosen area in (FIG. 2A); (FIG. 2G, FIG. 2H, FIG. 2I) images of displacement experiment.

DESCRIPTION OF THE INVENTION

Figures 1A, 1B, 1C, 1D, 1E, 1F, 1G, 1H:
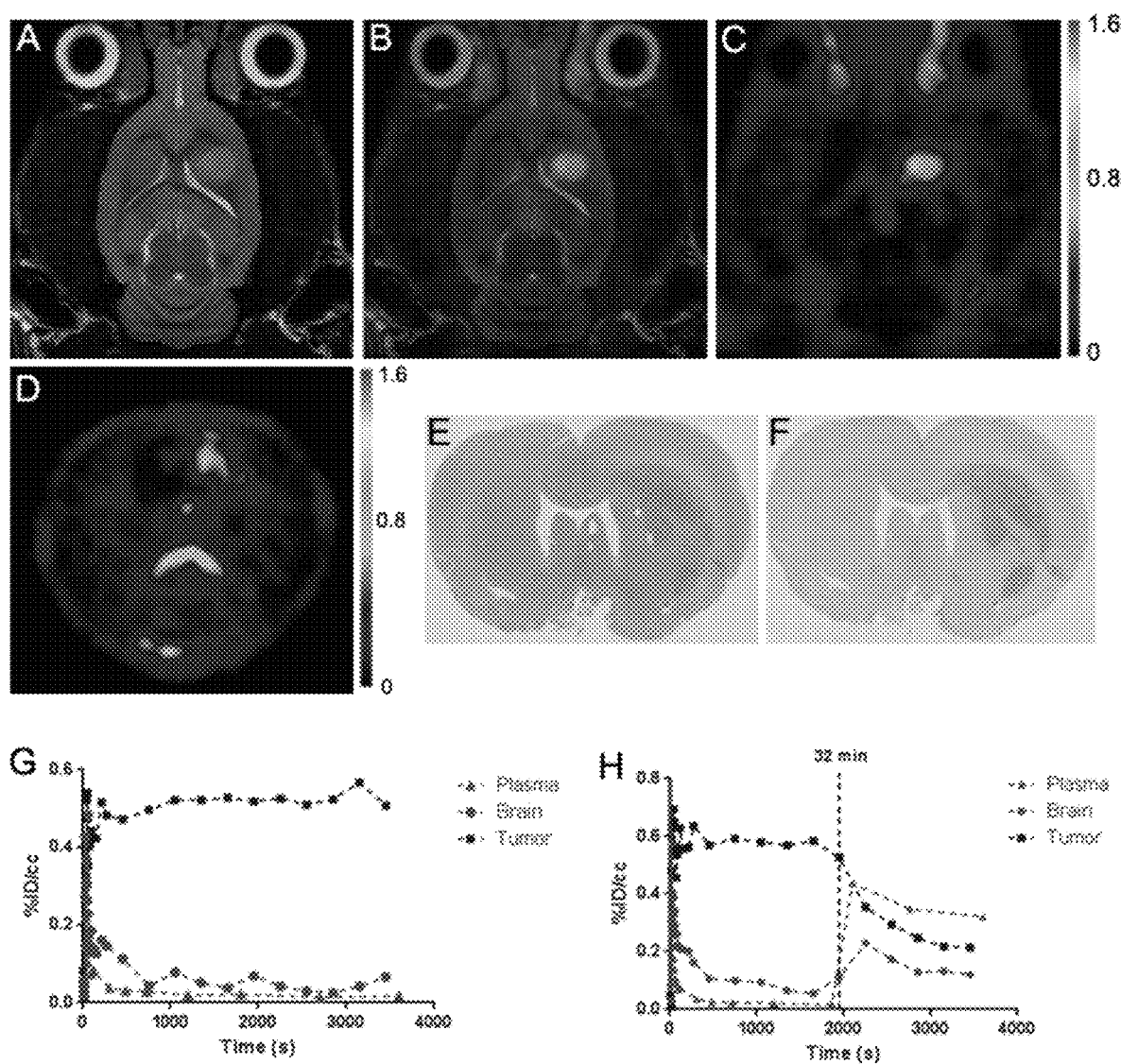
FIGS. 1A-1H shows imaging of preclinical glioma using an embodiment of the present invention. Specifically, imaging of preclinical glioma using [$^{18}$F]-14.

One aspect of the present invention is a method of imaging a molecular event in a sample, the method steps comprising administering to the sample a compound of the present invention having an affinity for a target. The probe has at least one of a ligand/signaling agent combination, or conjugable form of a ligand/signaling agent combination. After the probe is administered, a signal from the probe may be detected. In embodiments of the present invention, the sample can be at least one of cells, tissue, cellular tissue, serum, cell extract, bodily fluids. The bodily fluids may be, for example, breast milk, sputum, vaginal fluids, urine.

Another aspect of the present invention is a method of quantifying the progression of a disease state progression that includes the steps of (a) administering to a first sample a compound of the present invention that comprises a conjugable deoxythymidine compound and a signaling agent; (b) detecting a signal from the compound; (c) after a period of time from step (b), administering to a second sample a compound of the present invention, (d) detecting a second signal; and (e) comparing the first signal with the second signal to determine the progress of a disease state. Again examples of the sample are at least one of cells, tissue, cellular tissue, serum, cell extract, bodily fluids.

Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

By "disease" is meant any condition or disorder that damages or interferes with the normal function of a cell, tissue, organ or subject.

By "effective amount" is meant a quantity sufficient to produce a measurable difference, when compared with a control. For example, an amount sufficient to produce a measurable image, when the compound is used for imaging. Ultimately, the attending clinician will decide the appropriate amount and dosage regimen.

By "subject" is meant a mammal, including, but not limited to, a human or non-human mammal, such as a primate, rodent, bovine, equine, canine, ovine, deer, or feline.

Compounds

In one aspect, the invention relates to compounds, or pharmaceutically acceptable derivatives thereof, useful as imaging agents. In general, it is contemplated that each disclosed derivative can be optionally further substituted. It is also contemplated that any one or more derivative can be optionally omitted from the invention. It is understood that a disclosed compound can be provided by the disclosed methods or pharmaceutical compositions. It is also understood that each disclosed compound includes a pharmaceutically acceptable salt thereof. It is also understood that the disclosed compounds can be employed in the disclosed methods of using.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. Additionally, unless expressly described as "unsubstituted", all substituents, such as "phenyl," for example, can be substituted or unsubstituted.

Additionally, it is understood that the compounds described herein may have one or more charges atoms.

One embodiment of the present invention is a compound of the following formula, [$^{18}$F] VUIIS1008:

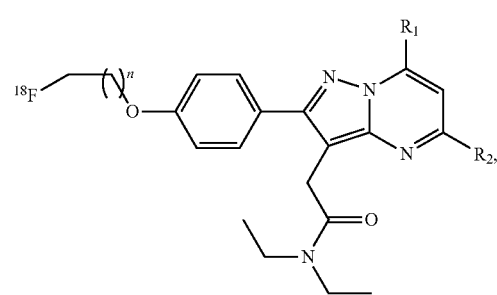

wherein $R_1$ and $R_2$ are independently $C_2$-$C_6$ alkyl, and n is an integer from 2-10. In a preferred embodiment, $R_1$ and $R_2$ are independently ethyl.

Another embodiment of the present invention is a compound of the following formula:

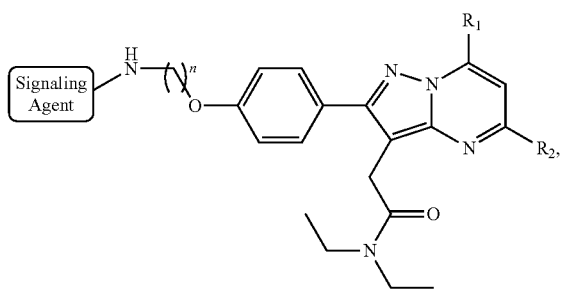

wherein $R_1$ and $R_2$ are independently $C_2$-$C_6$ alkyl. In a preferred embodiment, $R_1$ and $R_2$ are independently ethyl; and n is an integer from 2-10.

Another embodiment of the present invention is a compound of the following formula:

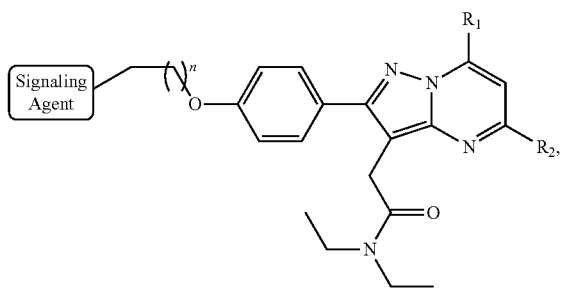

wherein $R_1$ and $R_2$ are independently $C_2$-$C_6$ alkyl. In a preferred embodiment, $R_1$ and $R_2$ are independently ethyl; and n is an integer from 2-10.

Another embodiment of the present invention is a compound of the following formula:

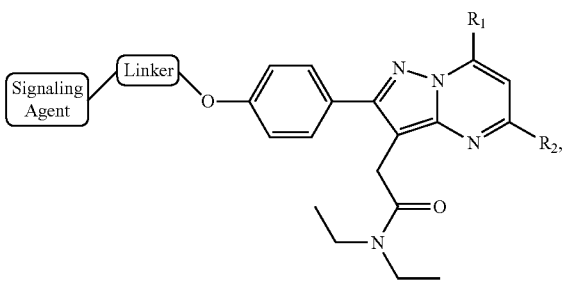

wherein $R_1$ and $R_2$ are independently $C_2$-$C_6$ alkyl. In a preferred embodiment, $R_1$ and $R_2$ are independently ethyl; and n is an integer from 2-10.

Another embodiment of the present invention is a compound of the following formula:

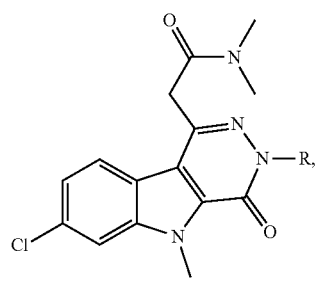

wherein R is phenyl, flourophenyl, nitrophenyl, pyridyl, fluoropyridyl, chloropyridyl, bromopyridyl.

In other embodiments, R is 2-flourophenyl.
In other embodiments, R is 3-flourophenyl.
In other embodiments, R is 4-flourophenyl.
In other embodiments, R is 2-pyridyl.
In other embodiments, R is 3-fluoro-2-pyridyl.
In other embodiments, R is 3-chloro-2-pyridyl.
In other embodiments, R is 3-bromo-2-pyridyl.

Another embodiment of the present invention is a compound of the following formula:

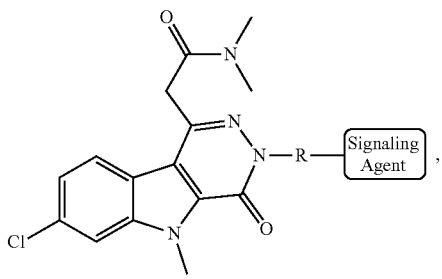

wherein R is phenyl, flourophenyl, nitrophenyl, pyridyl, fluoropyridyl, chloropyridyl, bromopyridyl.

The following are representative TSPO ligand scaffolds:

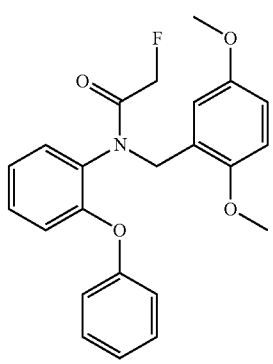

1

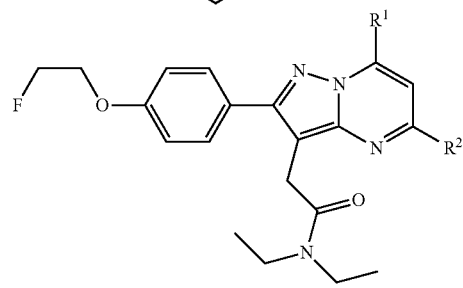

2a: $R^1 = R^2 =$ Methyl
2b: $R^1 = R^2 =$ Ethyl

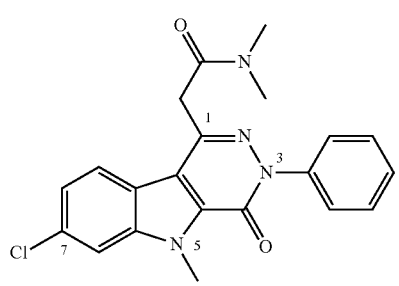

3

Aryloxyanilide (1, PBR06); Pyrazolopyrimidine (2a, DPA-714; 2b, VUIIS1008 (an embodiment of the present invention); Pyridazinoindole (3, SSR180575).

Compositions

The compounds of the present invention can be formulated into various compositions, for use in diagnostic or imaging methods, as well as treatment methods. The compositions of the present invention can be additionally assembled as a kit. Generally, a pharmaceutical composition comprises an effective amount (e.g., a detectable effective amount) of a compound described above.

A composition of the invention can be formulated as a pharmaceutical composition, which comprises a compound of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18$^{th}$ ed., Mack Publishing Company, 1990. The pharmaceutically acceptable carrier may also contain stabilizers, preservatives, antioxidants, or other additives, which are well known to one of skill in the art, or other vehicle as known in the art. Suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

In some embodiments, "pharmaceutically acceptable carrier" refers to a biocompatible solution, having due regard to sterility, p[Eta], isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like.

A pharmaceutical composition or kit of the invention can contain other pharmaceuticals or imaging agents, in addition to the compounds described herein. The other agents(s) can be administered at any suitable time during the imaging process, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

One skilled in the art will appreciate that a suitable or appropriate formulation can be selected, adapted or developed based upon the particular application at hand. Dosages for compositions of the invention can be in unit dosage form. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

Additionally, one skilled in the art can easily determine the appropriate dose, schedule, and method of administration for the exact formulation of the composition being used, in order to achieve the desired effective amount or effective concentration of the agent in the individual patient.

The dose of a composition of the invention, administered to an animal, particularly a human, in the context of the present invention should be sufficient to produce at least a detectable amount of a diagnostic or imaging response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, etc. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Other embodiments provide kits including a compound according to the invention. In certain embodiments, the kit provides packaged pharmaceutical compositions having a pharmaceutically acceptable carrier and a compound of the invention. In some embodiments the packaged pharmaceutical composition will include the reaction precursors necessary to generate the compound of the invention upon combination with a radionuclide. Other packaged pharmaceutical compositions provided by the present invention further include indicia such as at least one of: instructions for preparing compounds according to the invention from supplied precursors, instructions for using the composition to image cells or tissues expressing TSPO, or instructions for using the composition to image inflammation or neurodegeneration in a patient suffering, for example, an autoimmune disease, an inflammatory arthritides, a neurodegenerative disease, or atherosclerosis.

In certain embodiments, a kit according to the invention may contain, for example, from about 1 mCi to about 30 mCi of the radionuclide-labeled imaging agent described above, in combination with a pharmaceutically acceptable carrier. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. The kit may provide a compound of the invention in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form. Determination and optimization of such stabilizers and stabilization methods are well within the level of skill in the art.

Linker

Dyes (Signaling Agents)

With respect to the signaling agents used in connection with the present invention, embodiments include near infrared signaling agents. Also includes are dyes, such as, for example, near-infrared fluorophores/fluorescent dyes. Examples include cyanine dyes which have been used to label various biomolecules. See U.S. Pat. No. 5,268,486, which discloses fluorescent arylsulfonated cyanine dyes having large extinction coefficients and quantum yields for the purpose of detection and quantification of labeled components.

Additional examples include compounds of the following formulas:

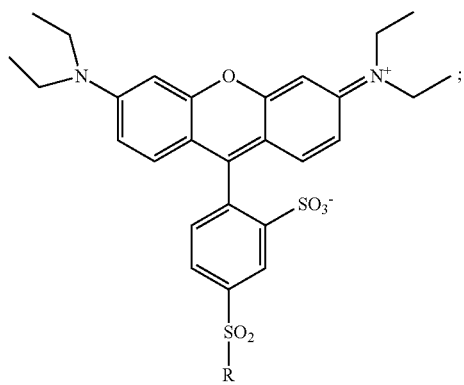

Lissamine-Rhodamine abs/em = 560nm, 590nm

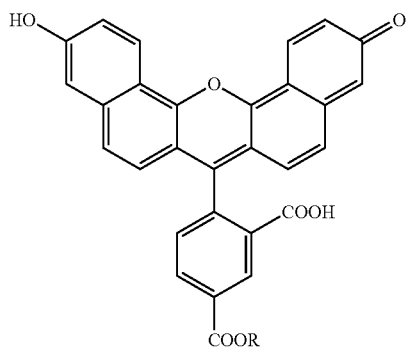

Carboxynaphthofluorescein abs/em = 580nm, 690nm

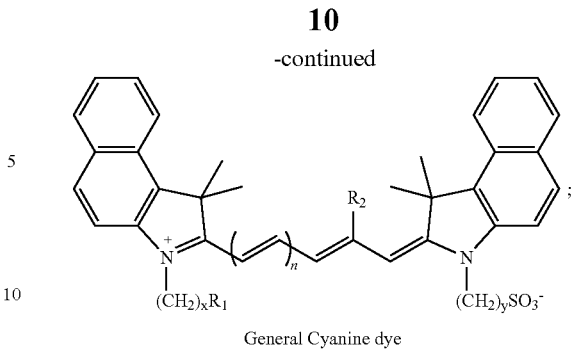

General Cyanine dye

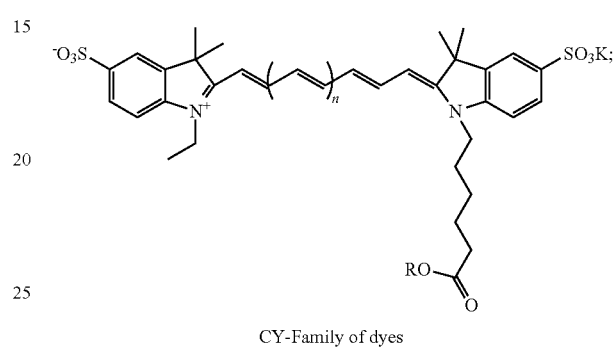

CY-Family of dyes and analogs thereof.

Additional examples include dyes available from Li-Cor, such as IR Dye 800CW™ available from Li-Cor.

Thus, examples of dyes for use in connection with the present invention include those disclosed in U.S. Pat. No. 6,995,274, the contents of which are incorporated herein by reference.

The following dye is a specific example:

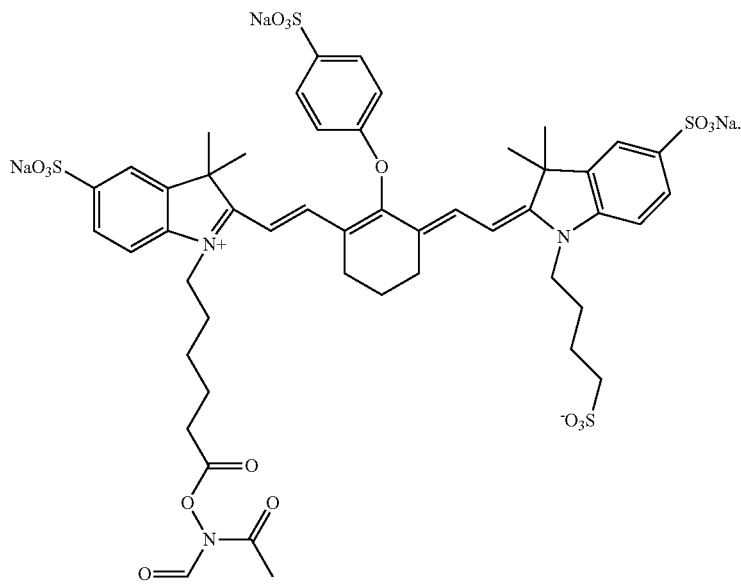

U.S. Pat. No. 6,995,274 additionally discloses the following dyes, all of which, when joined with a probe, are embodiments of the present invention:

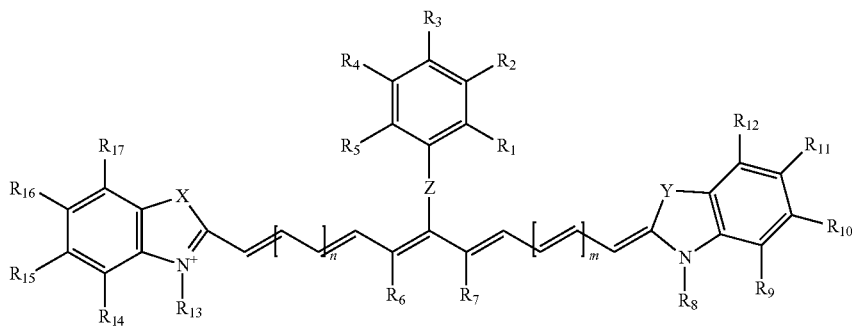

wherein, Z is a heteroatom having at least one lone pair of electrons. In one embodiment, Z is O, S, or $N_{35}$, wherein $R_{35}$ is H or alkyl. In embodiments, Z is of such a structure that only one atom is in the direct linkage between the benzene ring bonded to Z and to the polyene chain of: ⌢ bonded to Z. Side chains on the linkage between the benzene ring and the polyene chain are acceptable. In those embodiments having side chains, lower alkyl side chains may be used.

$R_1$-$R_5$ are each independently H, alkyl, halo, carboxyl, amino, or $SO_3$-$Cat^+$, wherein $Cat^+$ is a cation and at least one of $R_1$-$R_5$ is $SO_3$-$Cat^+$. In embodiments, $R_3$ is $SO_3$-$Cat^+$. In other embodiments, $Cat^+$ is $H^+$ or an alkali metal ion such as $Na^+$.

$R_6$ and $R_7$ are each H, alkyl, or optionally, together with the ⌢ group to which they are bonded, form a ring. In embodiments, $R_6$ and $R_7$ together with the atoms to which they are bonded form a ring. These rings may have 4 to 10 member atoms, more preferably 5 or 6 member atoms. In one embodiment, the ring including $R_6$ and $R_7$ is substituted, with, for example, a sulfonato radical.

The integers m and n are each independently integers from 0 to 5. In embodiments, both the sum of m and n is two. Additionally, the sum of m and n may be one. In other embodiments, both m and n are zero. As the sum of m and n rises, so too does the wavelength of the dye. Generally, the addition of each double bond in the polyene chain can increase the wavelength by about 40 to 120 nm. For the absorption changes accompanied with trimethine to pentamethine or pentamethine to heptamethine, there is a typically a bathochromic shift (red shift) of about 100 nm. For example, when m and n are both O, the wavelength of the preferred dye is about 770 nm. When m and n are both 1, the wavelength of the preferred dye is about 950 nm. The most preferred dyes operate in the NIR spectrum (600-1000 nm).

X and Y are each independently O, S, Se, or $CR_{19}R_{20}$, wherein $R_{19}$ and $R_{20}$ are each independently alkyl, or optionally form a ring together with the carbon atom to which they are bonded. In embodiments, X and Y are a heteroatom such as O, S, and Se. When X or Y is $CR_{19}R_{20}$, both $R_{19}$ and $R_{20}$ may be both lower alkyl, including methyl.

$R_8$ and $R_{13}$ are each independently alkyl, $(CH_2)_rR_{25}$ or $(CH_2)_rR_{19}$; wherein at least one of $R_8$ and $R_{13}$ is $(CH_2)_rR_{18}$ and wherein r is an integer from 1 to 50, and $R_{25}$ is a functional group that does not directly react with a carboxyl, hydroxyl, amino, or a thiol group, and $R_{18}$ is a functional group that can react with a carboxyl, hydroxyl, amino, or thiol group. In one embodiment, one of $R_8$ and $R_{13}$ is $(CH_2)_rR_{18}$ and the other is $(CH_2)_rR_{25}$. In other words, one of $R_8$ and $R_{13}$ reacts with a biomolecule to form a bond to that biomolecule, and that the other does not react. The $R_{18}$ group must be able to covalently bond with the biomolecule being labeled. $R_{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. $R_{25}$ groups include hydroxyl, thioacetyl, and sulfonato.

$R_9$-$R_{12}$ and $R_{14}$-$R_{17}$ are each independently H, alkyl, halo, amino, sulfonato, $R_{21}COOH$, $R_{21}OR_{22}$, $R_{21}SR_{22}$, or $R_{21}COOR_{22}$ wherein $R_{21}$ is a bond or alkylene and $R_{22}$ is alkyl, or optionally $R_{11}$ and $R_{12}$ together with the atoms to which they are bonded form an aromatic ring, or optionally $R_{16}$ and $R_{17}$ together with the atoms to which they are bonded form an aromatic ring. In one embodiment, one or both of $R_{11}$ and $R_{16}$ is sulfonato. In another embodiment, when $R_{11}$ and $R_{12}$ together with the atoms to which they are bonded form an aromatic ring, the ring is substituted in at least one position with a sulfonato group. In another embodiment, when $R_{16}$ and $R_{17}$ together with the atoms to which they are bonded form an aromatic ring, the ring is substituted in at least one position with a sulfonato group, a halo group, an alkyl substituent, or an amino substituent.

Another cyanine dye that can be used with the present invention is of the following formula:

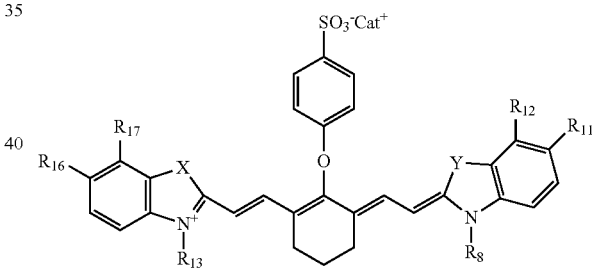

$Cat^+$ is a cation. In embodiments, $Cat^+$ is $H^+$ or a metal ion. More preferably, $Cat^+$ is an alkali metal ion, most preferably $Na^+$. X and Y are each independently O, S, Se, or $(CH_3)_2C$.

$R_8$ and $R_{13}$ are each independently alkyl, $(CH_2)_rR_{25}$ or $(CH_2)_rR_{19}$; wherein at least one of $R_8$ and $R_{13}$ is $(CH_2)_rR_{18}$ and wherein r is an integer from 1 to 50, and $R_{25}$ is a functional group that does not directly react with a carboxyl, hydroxyl, amino, or a thiol group, and $R_{18}$ is a functional group that can react with a carboxyl, hydroxyl, amino, or thiol group. In one embodiment, one of $R_8$ and $R_{13}$ is $(CH_2)_rR_{18}$ and the other is $(CH_2)_rR_{25}$. In other words, one of $R_8$ and $R_{13}$ reacts with a biomolecule to form a bond to that biomolecule, and that the other does not react. The $R_{18}$ group must be able to covalently bond with the biomolecule being labeled. $R_{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. $R_{25}$ groups include hydroxyl, thioacetyl, and sulfonato.

$R_{11}$ and $R_{12}$ are either H, sulfonato, or together with the atoms to which they are bonded form an aromatic ring. In a preferred embodiment, $R_{11}$ is sulfonato. In another preferred embodiment, when $R_{11}$ and $R_{12}$ together with the atoms to which they are bonded form an aromatic ring, the ring is substituted in at least one position with a sulfonato group.

$R_{16}$ and $R_{17}$ are either H, sulfonato, or together with the atoms to which they are bonded form an aromatic ring. In a preferred embodiment, $R_{16}$ is sulfonato. In another preferred embodiment, when $R_{16}$ and $R_{17}$ together with the atoms to which they are bonded form an aromatic ring, the ring is substituted in at least one position with a sulfonato group.

Further examples of cyanine dyes that can be used in connection with the present invention are those cyanine dyes that can be excited efficiently by commercially available equipment purchasable through companies such as Toshiba, Phillips, Blue Sky Research, and NEC.

Examples of how the above cyanine dyes may be prepared are shown in US 2004/0014981. That is, the cyanine dyes disclosed herein are prepared using methods that are well known in the art. Generally, cyanine dyes are prepared according to the procedures taught in Hamer, F. M., Cyanine Dyes and Related Compounds, Weissberger, M. A., ed. Wiley Interscience, N.Y. 1964. Further, U.S. Pat. Nos. 4,337,063; 4,404,289 and 4,405,711, incorporated herein by reference, describe a synthesis for a variety of cyanine dyes having N-hydroxysuccinimide active ester groups. U.S. Pat. No. 4,981,977, incorporated herein by reference, describes a synthesis for cyanine dyes having carboxylic acid groups. U.S. Pat. No. 5,268,486, incorporated herein by reference, discloses a method for making arylsulfonate cyanine dyes. U.S. Pat. No. 6,027,709, discussed below, and incorporated herein by reference, discloses methods for making cyanine dyes having phosphoramidite groups. U.S. Pat. No. 6,048,982, incorporated herein by reference, discloses methods for making cyanine dyes having a reactive group selected from the group consisting of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

Additional dyes that can be used with the present invention are the following:

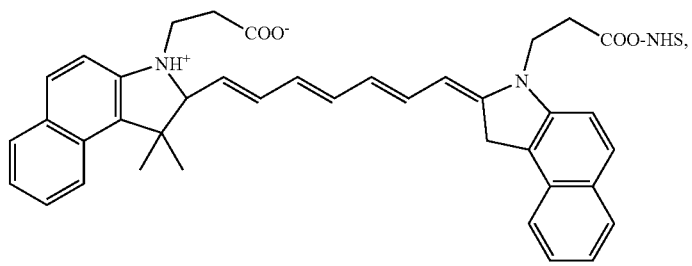

Cypate NHS-Achillifu

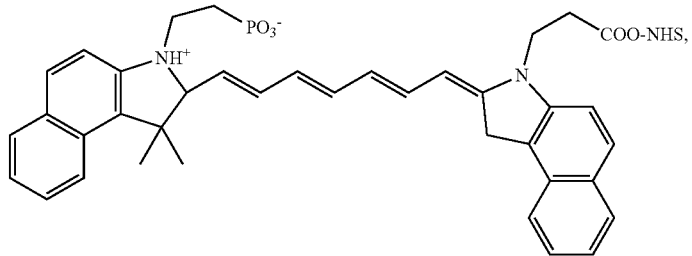

CY5.5-Amersham, Invitrogen

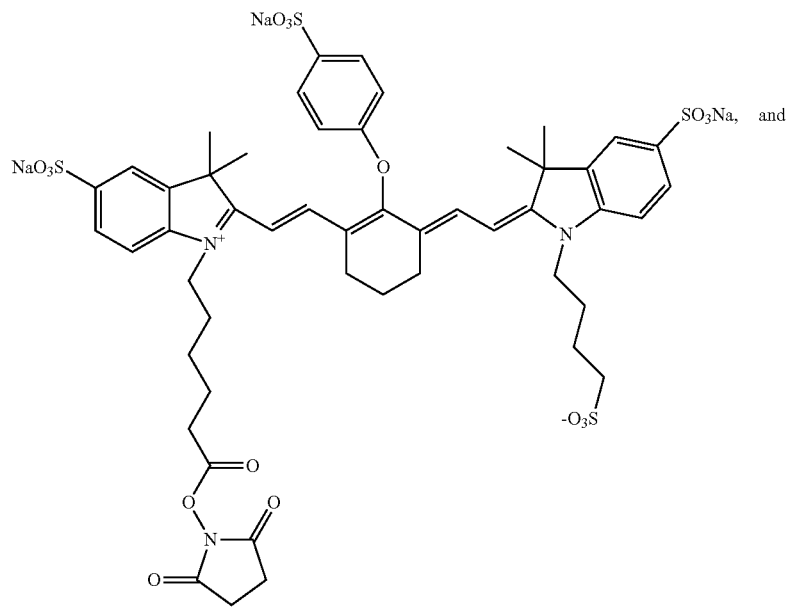

-continued

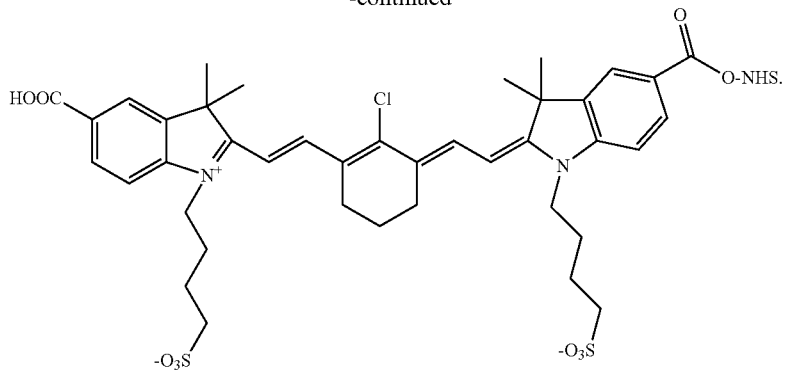

NIR-820 Pham, Tung et al.

Even further examples include the dyes disclosed in U.S. Pat. No. 6,027,709.

US '709 discloses dyes which have the following general formula:

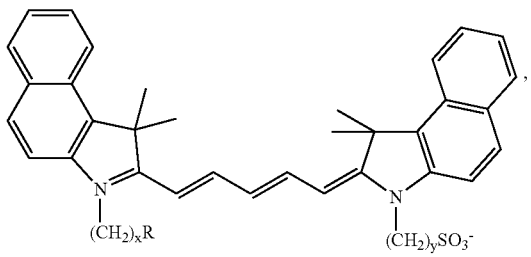

wherein R is —OH, —CO$_2$H, —NH$_2$, or —NCS and each of x and y, independently, is an integer selected from 1 to about 10. In preferred embodiments, each of x and y, independently, is an integer between about 2 and 6.

In one embodiment, the dye is N-(6-hydroxyhexyl)N'-(4-sulfonatobutyl)-3,3,3',3'-tetramethylbenz(e)indodicarbocyanine, which has the formula:

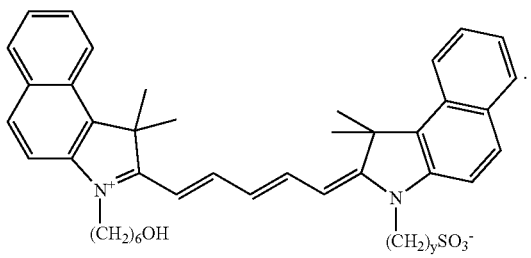

In a second embodiment, the dye is N-(5-carboxypentyl) N'-(4-sulfonatobutyl)3,3,3', 3'-tetramethylbenz(e)indodicarbocyanine, which has the formula:

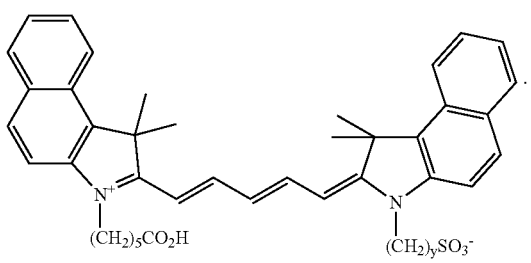

These two dyes are embodiments because they have commercially available precursors for the linking groups: 6-bromohexanol, 6-bromohexanoic acid and 1,4-butane sultone (all available from Aldrich Chemical Co., Milwaukee, Wis.). The linking groups provide adequate distance between the dye and the biomolecule for efficient attachment without imparting excessive hydrophobicity. The resulting labeled biomolecules retain their solubility in water and are well-accepted by enzymes.

These dyes, wherein R is —CO$_2$H or —OH can be synthesized, as set forth in detail in the US '709 patent, by reacting the appropriate N-(carboxyalkyl)- or N-(hydroxyalkyl)-1,1,2-trimethyl-1H-benz(e)indolinium halide, preferably bromide, with sulfonatobutyl-1,1,2-trimethyl-1H-benz (e)indole at a relative molar ratio of about 0.9:1 to about 1:0.9, preferably 1:1 in an organic solvent, such as pyridine, and heated to reflux, followed by the addition of 1,3,3-trimethoxypropene in a relative molar ratio of about 1:1 to about 3:1 to the reaction product and continued reflux. The mixture subsequently is cooled and poured into an organic solvent such as ether. The resulting solid or semi-solid can be purified by chromatography on a silica gel column using a series of methanol/chloroform solvents.

As an alternative, two-step, synthesis procedure, also detailed in U.S. '709, N-4-sulfonatobutyl-1,1,2-trimethyl-1H-benz(e)indole and malonaldehyde bis(phenylimine)-monohydrochloride in a 1:1 molar ratio can be dissolved in acetic anhydride and the mixture heated. The acetic anhydride is removed under high vacuum and the residue washed with an organic solvent such as ether. The residual solid obtained is dried and subsequently mixed with the appropriate N-(carboxyalkyl)- or N-(hydroxyalkyl)-1,1,2-trimethyl-1H-benz(e)indolinium halide in the presence of an organic solvent, such as pyridine. The reaction mixture is heated, then the solvent is removed under vacuum, leaving the crude desired dye compound. The procedure was adapted from the two step procedure set forth in Ernst, L. A., et al., Cytometry 10:3-10 (1989).

The dyes also can be prepared with an amine or isothiocyanate terminating group. For example, N-(omega.-aminoalkyl)-1,1,2-trimethyl-1H-benz(e)indolenium bromide hydrobromide (synthesized as in N. Narayanan and G. Patonay, J. Org. Chem. 60:2391-5 (1995)) can be reacted to form dyes of formula 1 wherein R is —NH$_2$. Salts of these amino dyes can be converted to the corresponding isothiocyanates by treatment at room temperature with thiophosgene in an organic solvent such as chloroform and aqueous sodium carbonate.

These dyes have a maximum light absorption which occurs near 680 nm. They thus can be excited efficiently by commercially available laser diodes that are compact, reliable and inexpensive and emit light at this wavelength. Suitable commercially available lasers include, for example, Toshiba TOLD9225, TOLD9140 and TOLD9150, Phillips CQL806D, Blue Sky Research PS 015-00 and NEC NDL 3230SU. This near infrared/far red wavelength also is advantageous in that the background fluorescence in this region normally is low in biological systems and high sensitivity can be achieved.

The hydroxyl, carboxyl and isothiocyanate groups of the dyes provide linking groups for attachment to a wide variety of biologically important molecules, including proteins, peptides, enzyme substrates, hormones, antibodies, antigens, haptens, avidin, streptavidin, carbohydrates, oligosaccharides, polysaccharides, nucleic acids, deoxy nucleic acids, fragments of DNA or RNA, cells and synthetic combinations of biological fragments such as peptide nucleic acids (PNAs).

In another embodiment of the present invention, the ligands of the present invention may be conjugated to a lissamine dye, such as lissamine rhodamine B sulfonyl chloride. For example, a conjugable form of DAA1106 may be conjugated with lissamine rhodamine B sulfonyl chloride to form a compound of the present invention.

Lissamine dyes are typically inexpensive dyes with attractive spectral properties. For example, examples have a molar extinction coefficient of 88,000 $cm^{-1}M^{-1}$ and good quantum efficient of about 95%. It absorbs at about 568 nm and emits at about 583 nm (in methanol) with a decent stokes shift and thus bright fluorescence.

Coupling procedures for the PBR ligands and Glucosamine proceed via standard methods and will be recognized by those skilled in the art. In general, the nucleophilic N terminus of the targeting moieties are reactive towards activated carbonyls, for example an NHS (N-hydroxysuccinimide ester), sulfonyl chlorides, or other electrophile bearing species. Solvent of choice for coupling reactions can be dye specific, but include dimethyl sulfoxide (DMSO), chloroform, and/or phosphate buffered saline (PBS buffer). The resulting conjugates, amides, sulfonamides, etc. resist hydrolysis under physiological conditions, and are thus useful for in-vivo and in-vitro application.

The following are examples of compounds of the present invention:

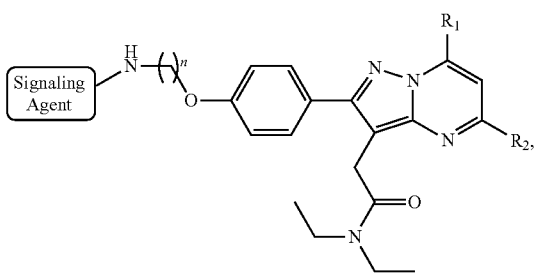

wherein $R_1$ and $R_2$ are independently $C_2$-$C_6$ alkyl. In a preferred embodiment, $R_1$ and $R_2$ are independently ethyl; and n is an integer from 2-10.

Another example is a compound of the following formula:

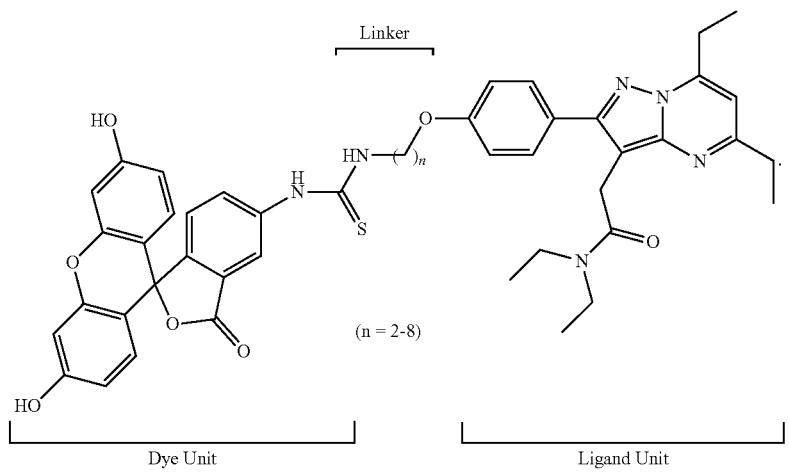

The following are examples of dyes in conjugable form

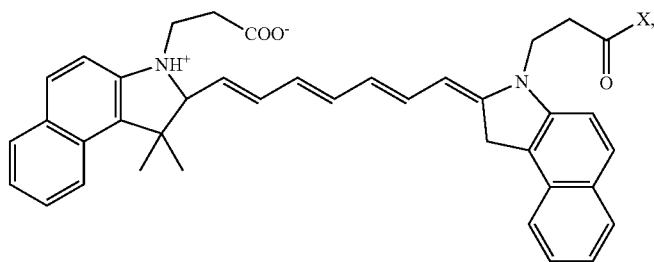

Cypate: X = Conjugation Site

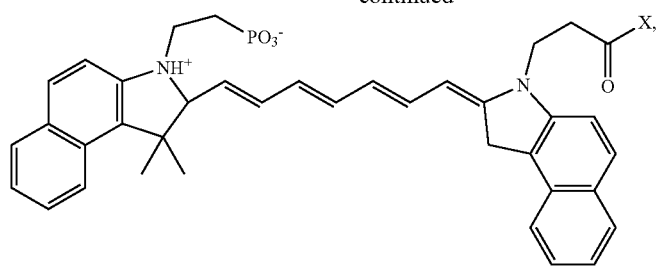
CY5.5: X = Conjugation Site
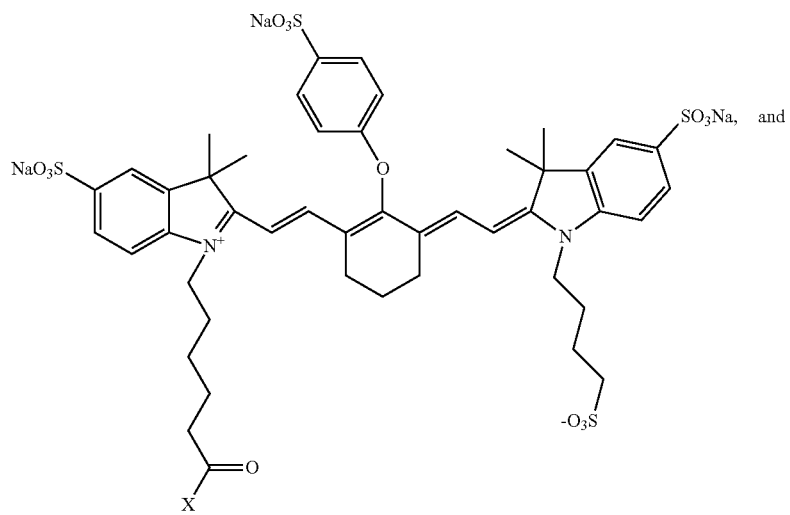
LI-COR 800CW: X Conjugation Site
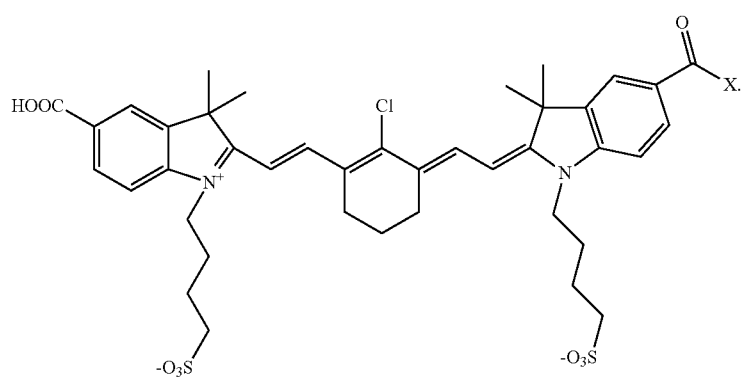
NIR-820: X Conjugation Site The following compound is an example of one of the coupled compounds described above:

Compound IV

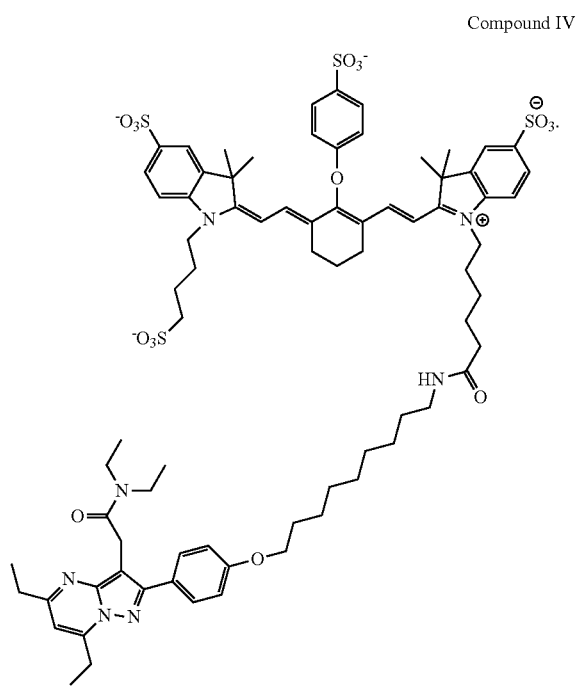

Uses

The compounds and compositions described above, including various radiolabeling options of the compounds and compositions described above, are useful for diagnostic or imaging purposes. The compounds and compositions may be used as imaging agents as described in US Patent Application Publication Number 2014/0322133, incorporated herein by reference.

Accordingly, embodiments include methods for imaging cells, tissues, a sample, an organ, a cell, or a subject by imaging the cells, the tissues, a sample, an organ or a subject which has or is suspected of having increased levels of translocator protein, TSPO, after administration of a detectably sufficient amount of a radioisotopically-enriched compound of the present invention.

Typically, the image indicates the level of TSPO protein, relative to the background. Regions of increased TSPO protein may be visualized by comparing them with the background level of TSPO protein in a particular culture, sample, organ, or subject. The background may be produced, for example, by non-specific binding of the compound to other proteins. TSPO protein levels below the level of detection will not be imaged. Likewise, TSPO levels below the level of background will not be imaged. Compounds of the invention are highly specific for TSPO, have minimal non-specific binding, and therefore a low background. Increased TSPO may be caused by increased expression of TSPO protein in the cells, tissues, sample, organ or subject being imaged. In other instances, TSPO protein may be produced elsewhere and migrate to the imaged cells, sample, organ or subject. Where elevated levels of TSPO are associated with cells, tissues, samples or organs, they may be imaged using the compounds and methods of the invention.

Embodiments include methods of imaging one or more cells, organs, tissues, samples or subjects by exposing cells to or administering to a subject a detectably effective amount of a compound with an isotopic label suitable for imaging. The cells, organs, tissues or samples may be imaged while within an organism, either by whole body imaging or intraoperative imaging, or may be excised from the organism for imaging. Cells may be imaged, for example, in culture, in a tissue, organ, or even in a subject. Cells may be imaged collectively. Cells or a sample may be imaged in vivo or in vitro, and may be, for example, a sample of an organ or other portion of an organism, or tissue samples grown in culture. In some cases, the sample may be removed from an organism prior to imaging. In some embodiments, organs or portions of organs may be removed prior to imaging, or imaged in vivo. Imaging organs means detecting or visualizing the organ, or portion of the organ associated with elevated levels of TSPO protein. In some inflammation, TSPO may be expressed by immune cells associated with the inflamed organ or tissue, but imaging these cells produces an image of the inflamed portion of the organ itself. All such uses are envisioned.

In general, any cells expressing or overexpressing TSPO may be imaged. In some embodiments, the cells are glial cells or immune cells. Glial cells include, for example, microglia, astrocytes, oligodendrocytes, ependymal cells or ependymocytes, radial glia, and Schwann cells. Immune cells include, for example, macrophages, monocytes, leukocytes, and lymphocytes. Other cells that may express or overexpress TSPO include, for example, steroidogenic cells such as testicular, adrenocortical, and brain glial tumor cells, and cancerous tissues of the breast, ovary, colon, prostate, and brain. In some embodiments, the organ being imaged is the brain. In some embodiments, the organ being imaged is the lungs. In some embodiments, the organ being imaged is the heart. In other embodiments, organs (e.g. spleen) and tissues of the lymphatic system may be imaged.

Additionally, any condition associated with TSPO expression may be imaged in a subject. In some embodiments, the subject has inflammation. In some embodiments, the subject has an autoimmune disease. In some embodiments, the subject has inflammatory arthritis. In some embodiments, the subject has a neurodegenerative disease. In some embodiments, the subject has atherosclerosis. Other conditions that may be associated with TSPO expression include neuropathological conditions including stroke, herpes and HIV encephalitis, and neurodegenerative disorders such as Alzheimer's disease, multiple sclerosis, amyotrophic lateral sclerosis, Parkinson's disease, and Huntington's disease, and other conditions such as myocarditis, pneumonitis, and pneumonia.

In some embodiments, the subject is a human, rat, mouse, cat, dog, horse, sheep, cow, monkey, avian, or amphibian. In another embodiment, the cell is in vivo or in vitro. Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood, urine or tissue samples of the animals mentioned for veterinary applications. In other in vitro applications, the cells or tissues are present in culture or in suspension.

Imaging agents of the invention may be used in accordance with the methods of the invention by one of skill in the art. Images can be generated by virtue of differences in the spatial distribution of the imaging agents which accumulate at a site when contacted with TSPO. The spatial distribution may be measured using any means suitable for the particular label, for example, a gamma camera, a PET apparatus, a SPECT apparatus, and the like. The extent of accumulation of the imaging agent may be quantified using known methods for quantifying radioactive emissions.

In general, a detectably effective amount of the imaging agent is administered to a subject. As used herein, "a detectably effective amount" of the imaging agent is defined as an amount sufficient to yield an acceptable image using equipment which is available for clinical use. A detectably effective amount of the imaging agent may be administered in more than one dose. The imaging agent can be administered in any suitable to result in delivery to the site where TSPO accumulation may be expected to occur. Examples of administration include ingestion or injection, including, for example, interperitoneal injection or intravenous injection.

The detectably effective amount of the imaging agent can vary according to factors such as the degree of susceptibility of the individual, the age, sex, and weight of the individual, idiosyncratic responses of the individual, and the dosimetry. Detectably effective amounts of the imaging agent can also vary according to instrument and film-related factors. Optimization of such factors is well within the level of skill in the art. The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

Thus, embodiments of the present invention include methods of imaging. Embodiments include methods where imaging is performed by autoradiography, single photon emission computed tomography, or positon emission tomography. In some embodiments, the imaging is autoradiography. In some embodiments, imaging is single photon emission computed topography and the compound of the present invention is radiolabeled.

In some embodiments, the cells being imaged are glial cells or immune cells.

In some embodiments, the organ being imaged is the brain. In some embodiments, the organ being imaged is the lungs. In some embodiments, the organ being imaged is the heart.

In some embodiments, the subject being imaged has inflammation. In some embodiments, the subject being imaged has an autoimmune disease. In some embodiments, the subject being imaged has a neurodegenerative disease. In some embodiments, the subject being imaged is atherosclerosis. In some embodiments, the subject being imaged has a tumor. In some embodiments, the subject being imaged has myocarditis. In some embodiments, the subject being imaged has pneumonitis. In some embodiments, the subject being imaged has pneumonia.

Additionally, the compounds and compositions are useful as drug delivery agents. More specifically, embodiments of the present invention are compounds and methods of treating cancer comprising administering a conjugate of the present invention. See U.S. Pat. No. 8,372,868 for examples of TSPO probe selective drug delivery.

Etoposide, for example, is one of the most widely used anticancer drugs and is active against small-cell lung cancers, leukemias, and lymphomas.

Etoposide compound

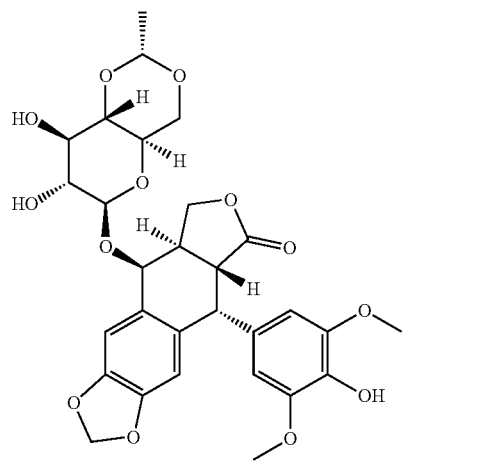

However, the application of etoposide in cancer therapy is limited by the lack of selectivity. PBR is a mitochondrial protein and highly expressed in leukemia and lymphoma cells. DAA1106 is a relatively new PBR ligand with fentomolar ($10^{-15}$ M) binding affinity for PBR. An embodiment of the present invention is coupling etoposide and other cancer therapeutics to DAA1106, and the resulting molecules can provide selective cancer therapy.

Accordingly, an embodiment of the present invention is a compound of the following formula:

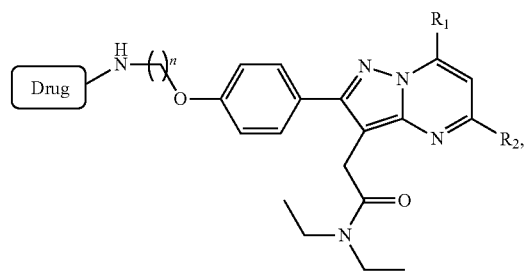

wherein $R_1$ and $R_2$ are independently $C_2$-$C_6$ alkyl. In a preferred embodiment, $R_1$ and $R_2$ are independently ethyl; and n is an integer from 2-10.

Accordingly, an embodiment of the present invention is a compound of the following formula:

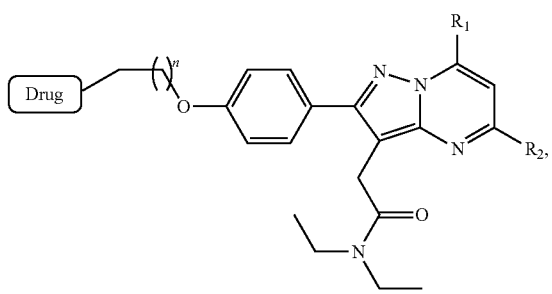

wherein $R_1$ and $R_2$ are independently $C_2$-$C_6$ alkyl. In a preferred embodiment, $R_1$ and $R_2$ are independently ethyl; and n is an integer from 2-10.

Another embodiment of the present invention is a compound of the following formula:

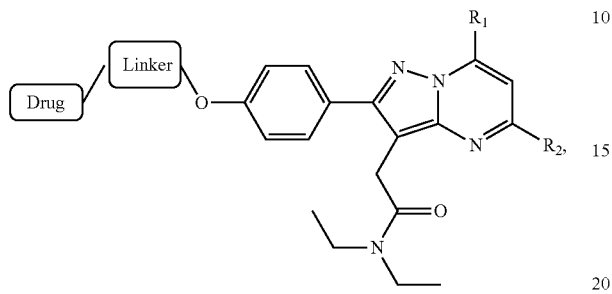

wherein $R_1$ and $R_2$ are independently $C_2$-$C_6$ alkyl. In a preferred embodiment, $R_1$ and $R_2$ are independently ethyl.

In embodiments of the present invention, a chemotherapeutic agent is the "drug." An embodiment of the chemotherapeutic agent is a topoisomerase inhibitor. A topoisomerase inhibitor may be adriamycin, amsacrine, camptothecin, daunorubicin, dactinomycin, doxorubicin, eniposide, epirubicin, etoposide, idarubicin, mitoxantrone, teniposide, or topotecan. Preferably, the topoisomerase inhibitor is etoposide.

Accordingly, another embodiment of the present invention is a compound of the following formula:

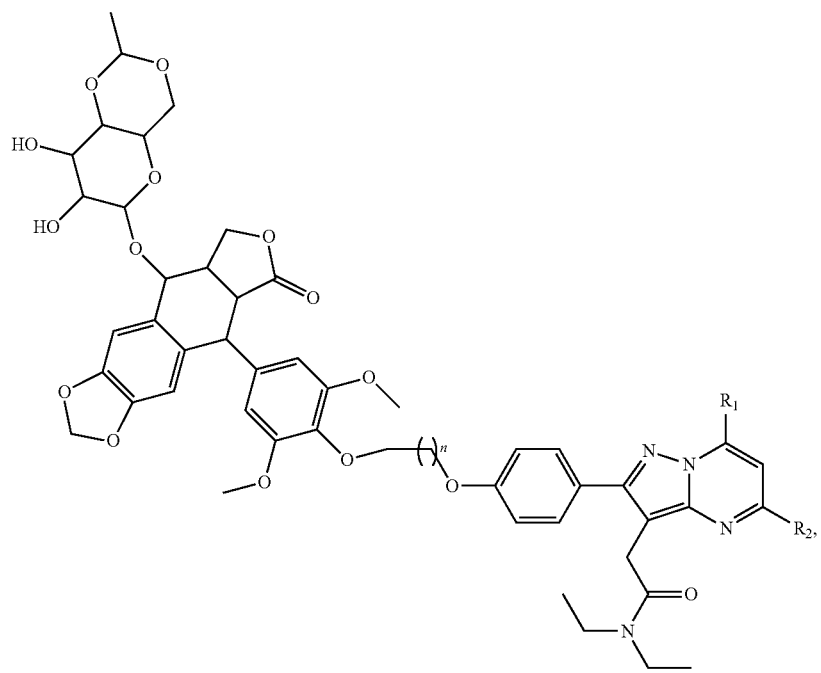

wherein $R_1$ and $R_2$ are independently $C_2$-$C_6$ alkyl. In a preferred embodiment, $R_1$ and $R_2$ are independently ethyl.

Another embodiment of the present invention is a compound of the following formula:

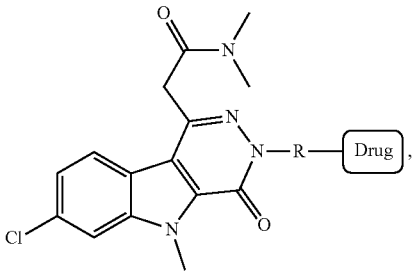

wherein R is phenyl, flourophenyl, nitrophenyl, pyridyl, fluoropyridyl, chloropyridyl, bromopyridyl.

Another embodiment of the present invention is a compound of the following formula:

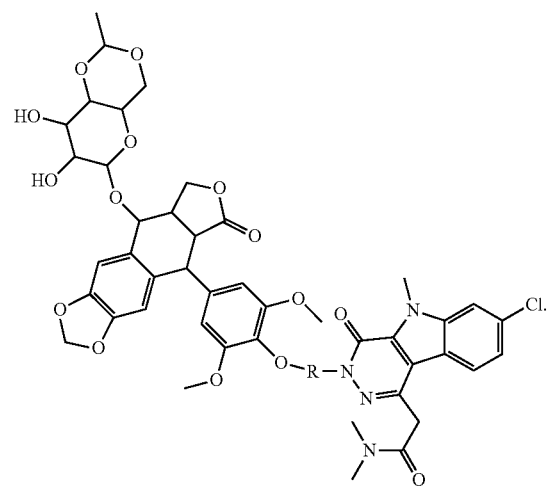

The imaging and/or therapeutic agents of the present invention may be administered as determined by one of ordinary skill in the art. In embodiments the agents may be administered as shown in U.S. application Ser. No. 11/181,201, incorporated herein by reference.

That is, compounds of the present invention can be administered orally, parenterally by intravenous injection, transdermally, by pulmonary inhalation, by intravaginal or intrarectal insertion, by subcutaneous implantation, intramuscular injection or by injection directly into an affected tissue, as for example by injection into a tumor site. In some instances the materials may be applied topically at the time surgery is carried out. In another instance the topical administration may be ophthalmic, with direct application of the therapeutic composition to the eye.

The materials are formulated to suit the desired route of administration. The formulation may comprise suitable excipients include pharmaceutically acceptable buffers, stabilizers, local anesthetics, and the like that are well known in the art. For parenteral administration, an exemplary formulation may be a sterile solution or suspension; For oral dosage, a syrup, tablet or palatable solution; for topical application, a lotion, cream, spray or ointment; for administration by inhalation, a microcrystalline powder or a solution suitable for nebulization; for intravaginal or intrarectal administration, pessaries, suppositories, creams or foams. Preferably, the route of administration is parenteral, more preferably intravenous.

In general, an embodiment of the invention is to administer a suitable daily dose of a therapeutic composition that will be the lowest effective dose to produce a therapeutic effect. However, it is understood by one skilled in the art that the dose of the composition to practice the invention will vary depending on the subject and upon the particular route of administration used. It is routine in the art to adjust the dosage to suit the individual subjects. Additionally, the effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The actual dosage suitable for a subject can easily be determined as a routine practice by one skilled in the art, for example a physician or a veterinarian given a general starting point.

The therapeutic treatment may be administered hourly, daily, weekly, monthly, yearly (e.g., in a time release form) or as a one-time delivery. The delivery may be continuous delivery for a period of time, e.g., intravenous delivery. In one embodiment of the methods described herein, the therapeutic composition is administered at least once per day. In one embodiment, the therapeutic composition is administered daily. In one embodiment, the therapeutic composition is administered every other day. In one embodiment, the therapeutic composition is administered every 6 to 8 days. In one embodiment, the therapeutic composition is administered weekly.

In embodiments of the methods described herein, the route of administration can be oral, intraperitoneal, transdermal, subcutaneous, by vascular injection into the tumor, by intravenous or intramuscular injection, by inhalation, topical, intralesional, infusion; liposome-mediated delivery; intrathecal, gingival pocket, rectal, intrabronchial, nasal, transmucosal, intestinal, ocular or otic delivery, or any other methods known in the art as one skilled in the art may easily perceive. In other embodiments of the invention, the compositions incorporate particulate forms protective coatings, hydrolase inhibitors or permeation enhancers for various routes of administration, including parenteral, pulmonary, nasal and oral.

An embodiment of the method of present invention is to administer the compositions described herein in a sustained release form. Such method comprises implanting a sustained-release capsule or a coated implantable medical device so that a therapeutically effective dose is continuously delivered to a subject of such a method. The compositions may be delivered via a capsule which allows sustained-release of the agent or the peptide over a period of time. Controlled or sustained-release compositions include formulation in lipophilic depots (e.g., fatty acids, waxes, oils). Also comprehended by the invention are particulate compositions coated with polymers (e.g., poloxamers or poloxamines).

The method of present invention is effective in treatment of various types of cancers, including but not limited to: pancreatic cancer, renal cell cancer, Kaposi's sarcoma, chronic leukemia (preferably chronic myelogenous leukemia), chronic lymphocytic leukemia, breast cancer, sarcoma, ovarian carcinoma, rectal cancer, throat cancer, melanoma, colon cancer, bladder cancer, lymphoma, mesothelioma, mastocytoma, lung cancer, liver cancer, mammary adenocarcinoma, pharyngeal squamous cell carcinoma, gastrointestinal cancer, stomach cancer, myeloma, prostate cancer, B-cell malignancies or metastatic cancers.

The present invention is also effective against other diseases related to unwanted cell proliferation. Such hyperproliferative diseases include but are not limited to: psoriasis, rheumatoid arthritis, lamellar ichthyosis, epidermolytic hyperkeratosis, restenosis, endometriosis, proliferative retinopathy, lung fibrosis, desmoids or abnormal wound healing.

EXAMPLE

This Example demonstrates imaging embodiments of the present invention.

The present inventors previously reported the first utilizations of two TSPO-specific PET ligands for quantitative assessment of TSPO expression in preclinical glioma, the aryloxyanilide N-[$^{18}$F]fluoroacetyl-N-(2,5-dimethoxybenzyl)-2-phenoxyaniline ([$^{18}$F]PBR06, [$^{18}$F]-1),[11] and the pyrazolopyrimidine N,N-diethyl-2-(2-(4-(2-[$^{18}$F]fluoroethoxy)phenyl)-5,7-dimethylpyrazolo[1,5-a]pyrimidin-3-yl)acetamide ([$^{18}$F]DPA-714, [$^{18}$F]-2a)[12].

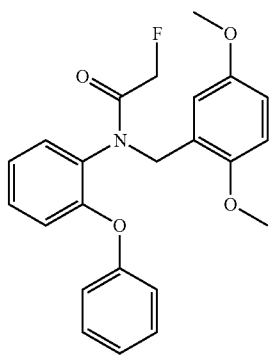

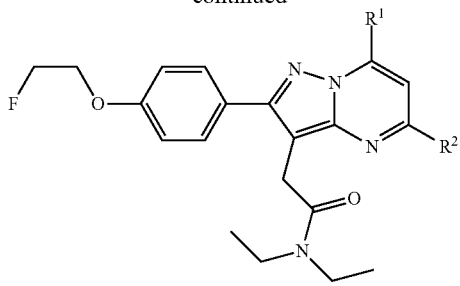

2a: R¹ = R² = Methyl
2b: R¹ = R² = Ethyl

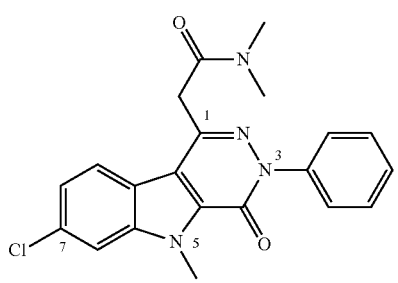

3

Through focused library synthesis and structure—activity relationship (SAR) development of the 5,6,7-substituted pyrazolopyrimidine scaffold of [¹⁸F]-2a, the inventors developed 2-(5,7-diethyl-2-(4-(2-[¹⁸F]fluoroethoxy)phenyl) pyrazolo[1,5-a]pyrimidin-3-yl)-N,N-diethylacetamide ([¹⁸F]-2b, [¹⁸F]VUIIS1008), a novel and highly potent TSPO PET ligand exhibiting a 36-fold enhancement in affinity compared to [¹⁸F]-2a and accessible in high radiochemical yield and specific activity.[13] Subsequent in vivo studies of [¹⁸F]-2b demonstrated this agent to possess several properties for molecular imaging of TSPO-expressing cancers.[13,21]

In addition to the aryloxyanilides and pyrazolopyrimidines, pyridazinoindoles are another series of potent TSPO ligands, as represented by 7-chloro-N,N,5-trimethyl-4-oxo-3-phenyl-3,5-dihydro-4H-pyridazino[4,5-b]indole-1-acetamide (SSR180575, 3).[22,23] Developed originally by Sanofi-Aventis, the specificity and high-affinity of 3 for TSPO has prompted research in cardiovascular[24,25] and renal pathologies,[26] as well as neurodegenerative indications,[23] inflammatory disorders,[22,27-29] and HIV pathogenesis.[30]

The present inventors determined that optimization of 3, specifically at the N3 position, would yield TSPO ligands with comparable affinity and potential to serve as PET imaging ligands. These experiments led to the synthesis of 3 in only four steps and the subsequent development of 7-chloro-N,N,5-trimethyl-4-oxo-3(6-fluoropyridin-2-yl)-3,5-dihydro-4H-pyridazino[4,5-b]indole-1-acetamide (14), a novel pyridazinoindole TSPO ligand exhibiting binding comparable to 3 and structural features suitable for radiolabeling with fluorine-18 (¹⁸F). Radiofluorination of either the 2-chloro (15) or 2-bromo (16) precursor gave 7-chloro-N,N,5-trimethyl-4-oxo-3(6-[¹⁸F]fluoropyridin-2-yl)-3,5-dihydro-4H-pyridazino[4,5-b]indole-1-acetamide ([¹⁸F]-14), which was subsequently evaluated in vivo in a preclinical model of glioma (C6). [¹⁸F]-14 exhibited modest accumulation in normal brain, yet robust accumulation in tumor tissue, which facilitated excellent imaging contrast. [¹⁸F]-14 was fully displaceable by administration of non-radioactive 14 halfway through the PET scan. Overall, the present invention shows compounds of the present invention, including [¹⁸F]-14 as a promising, novel PET ligand for evaluating TSPO expression in gliomas and potentially other solid tumors and diseases.

The original synthesis of SSR180575 (3) remains a known process at seven total steps.[31] Moreover, previous SAR studies of 3 targeted four areas on the scaffold, the acetamide functionality at C1 and the N3, N5, and C7 positions of the tricyclic pyridazinoindole ring.[31,32] The synthesis developed and reported herein requires only four steps from a commercially available starting material (Scheme 1). Ppyridazinoindole embodiments of the present invention (Table 1) was assembled, with the point of divergence at the final condensation step with strategic arylhydrazines (8) (Scheme 1). The design of the library focused primarily on incorporation of fluorine onto an aromatic ring and potential substituents that would facilitate radiolabeling with ¹⁸F.

Scheme 1

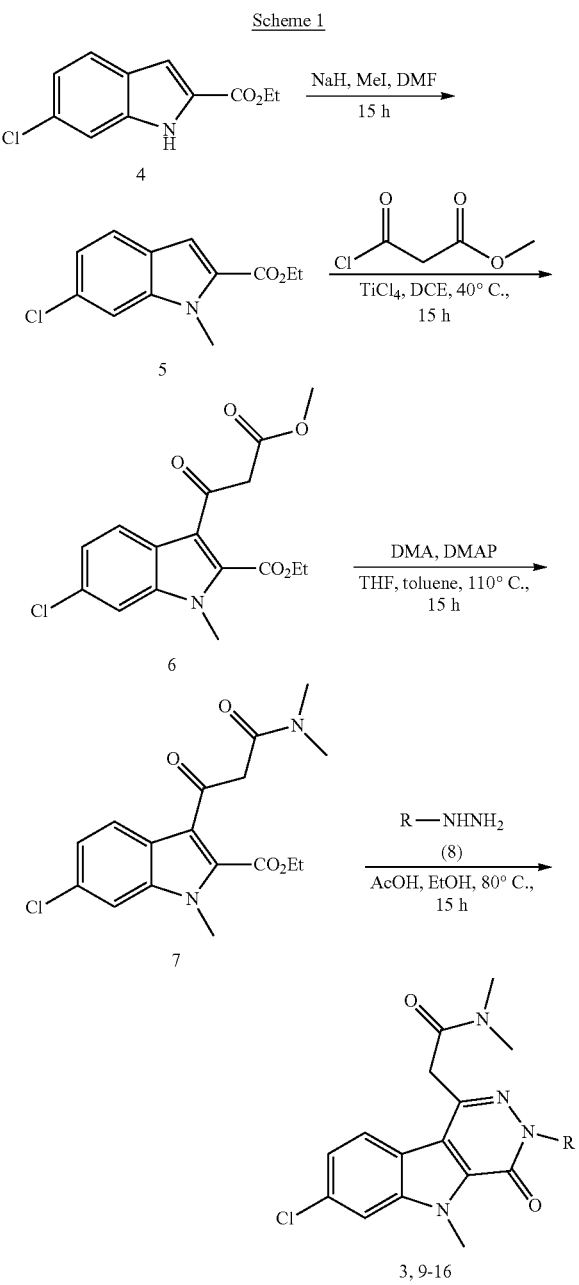

3, 9-16

TABLE 1

[Chemical structure: A chlorinated pyridazino-indole compound with N,N-dimethylacetamide substituent and N-R group]

| Compd | R | C6 Glioma Ki (pM)[b] | Heart Ki (pM)[b] | Kidney Ki (pM)[b] |
|---|---|---|---|---|
| 3[a] | Ph | 1.23 ± 0.08 | 0.762 ± 0.15 | 0.596 ± 0.04 |
| 9 | 2-fluorophenyl | 0.422 ± 0.06 | 0.591 ± 0.10 | 1.18 ± 0.04 |
| 10 | 3-fluorophenyl | 0.280 ± 0.07 | 0.180 ± 0.02 | 0.212 ± 0.02 |
| 11 | 3-nitrophenyl | 0.889 ± 0.2 | 1.18 ± 0.09 | 0.678 ± 0.2 |
| 12 | 4-fluorophenyl | 0.671 ± 0.2; 3020 ± 1007[d] | 0.877 ± 0.03 | 0.459 ± 0.03; 969 ± 752[d] |
| 13 | 2-pyridyl | 2409 ± 795.4 | 4936 ± 662.3 | 6796 ± 830.9 |
| 14[c] | 3-fluoro-2-pyridyl | 1.19 ± 0.05; 1770 ± 232.6[d] | 3.21 ± 0.4 | 2.21 ± 0.4 |
| 15 | 3-chloro-2-pyridyl | 2.34 ± 0.4 | 0.676 ± 0.08 | 0.495 ± 0.03 |
| 16 | 3-bromo-2-pyridyl | 1.48 ± 0.2 | 0.281 ± 0.01 | 0.965 ± 0.02 |

[a]SSR180575.
[b]Ki ± S.E.M. versus [$^3$H]PK11195.
[c]Ki versus [$^3$H]flunitrazepam in rat brain lysate >10 μM.
[d]Mixed affinity binding. All lysates procured from athymic nude rats. All experiments performed in triplicate.

The overall synthetic methodology is presented in Scheme 1. Starting from a commercially available indole (4), deprotonation with sodium hydride in DMF, followed by treatment with methyl iodide, gave the desired N-methylated intermediate (5) (85%). Acylation of (5) at C3 was achieved using TiCl$_4$ and methyl chloro-3-oxopropanoate in dichloroethane at 40° C. for 15 h, which gave keto diester 6 (46%). The necessary N,N-dimethylamide moiety at C1 (7) was achieved through displacement of the methoxy group of (6) with dimethylamine in toluene and THF in a sealed tube at 110° C. for 15 h. Final condensation with phenylhydrazine (8, R=phenyl) gave the lead compound, SSR1805875 (3), in 32% yield. To date, this stands as the shortest reported synthesis of this particular TSPO ligand.

Diversification at the N3 position of 3 was achieved through condensation of key intermediate 7 with a series of monosubstituted aryl hydrazines (8) (31-50%). The hydrazines chosen focused upon variation of the endogenous N3-phenyl ring, with particular attention towards preliminary SAR and functional groups amenable to PET ligand development, namely the presence of a fluorine atom and groups that would facilitate radiolabeling with $^{18}$F through an ipso-type substitution. The groups explored included: a substituted phenyl ring (2-, 3-, 4-positions) (9-12); a 2-pyridyl ring (13); a substituted 2-pyridyl ring (14-16).

Biological Testing and SAR

TSPO Binding Affinity: To evaluate binding to TSPO, radiometric binding assays were carried out with the compounds in a variety of athymic nude rat cell lysates (C6, heart, kidney) using N-(sec-butyl)-1-(2-chlorophenyl)-N-methyl-[$^3$H]-isoquinoline-3-carboxamide ([$^3$H]PK11195).[11,12] For central benzodiazepine receptor (CBR) binding, radioligand displacement was carried out against [$^3$H]flunitrazepam in healthy, athymic nude rat brain lysate. Affinities are expressed as K$_i$±S.E.M. (pM) in Table 1. All experiments were performed in triplicate.

Of the examples of the present invention specifically described herein, seven proved extremely potent in all three lysates, with K$_i$ values comparable to those of the parent SSR180575 (3): in C6 lysate, 0.280-2.34 pM versus 1.23 pM for 3; in heart 0.180-3.21 pM versus 0.762 pM for 3; in kidney, 0.212-2.21 pM versus 0.596 pM for 3. Only one analog, compound 13, bearing a 2-pyridyl ring at N3, did not appreciably bind TSPO in any of the lysates. Interestingly, a portion of the compounds synthesized showed evidence of mixed (low, high) binding affinities. In C6 lysate, compounds 12 and 14 demonstrated high-affinity binding at 0.671 and 1.19 pM, and low-affinity binding at 1770 and 3020 pM, respectively. Compound 12 demonstrated similar mixed binding in kidney lysate (0.459 and 969 pM), but not the heart. While multiple PK11195 TSPO binding sites have been reported and merit consideration,[33] recent research has also implicated a genetic polymorphism for such binding variations in the human brain.[34,35] However, genetic sequencing of the C6 cell line from the specific clonal population used for this study confirmed its wild-type status. The mixed binding we observed could potentially be a result of overlapping points of interaction that the analogs and PK11195 possess for TSPO.

SAR Analysis: Overall, the modifications made to lead compound 3, with the exception of 13, were well tolerated. While substitution of the N3-phenyl ring with 2-pyridine did adversely affect binding across all three lysates, comparable biological activity was regained with halogen substitution at the 3-position of the ring (14-16). This influence on potency could be attributed to an electronic effect of the halogen atom and merits further consideration in future studies. Similarly, 2-, 3-, and 4-fluorosubstitution on the endogenous phenyl ring with fluorine (9, 10, 12, respectively) proved to minimally affect TSPO affinity, as did 4-nitro-substitution (11). This series of compounds are among the most potent ligands reported for TSPO in C6 glioma (1 K$_i$=6170 pM;[11] 2a K$_i$=9730 pM;[12] 2b K$_i$=270 pM[13]). Moreover, in our lab, compound 14 represents a 1000-fold increase in potency over 2b.

PET Tracer Selection: Of the synthesized series, the 3-fluoro analog 10 was initially considered the candidate PET tracer, particularly given its activity and ready availability of its 3-nitro precursor (11). However, effective substitution of a nitro group with $^{18}$F$^-$ on a benzene ring requires a highly deactivated ring system, preferably with electron-withdrawing groups either ortho or para to the nitro moiety. Neither was the case for 11 as a precursor. Similar arguments could also be made for consideration of 9 or 12 as PET tracer candidates. Compound 14 was ultimately chosen as the candidate PET tracer, with 15 and 16 as possible precursors. The selectivity of 14 for TSPO over CBR was evaluated through displacement of [$^3$H]flunitrazepam in rat cerebral cortex membranes (Table 1). The selectivity of 14 for TSPO over CBR was verified with [$^3$H]flunitrazepam, which gave a K$_i$>10 μM.

Radiochemistry

Precursor Preparation and Radiosynthesis: Isotopic labeling of 3 with both $^{11}$C and $^{18}$F has been previously reported in the patent literature.[36] In the research literature, Thominiaux et al. reported $^{11}$C labeling at the 5-methylpyridazino[4,5-b]indole ([indole-N-methyl-$^{11}$C]SSR180575) and N,N-dimethylacetamide ([acetamide-N-methyl-$^{11}$C]SSR180575)[37] moieties. Within the context of radiochemical yield and purity, and in vivo pharmacological properties, [indole-N-methyl-$^{11}$C]SSR180575 was advanced as a candidate for imaging neuroinflammation[37] and afforded higher image contrast when compared to the traditional isoquinoline [$^{11}$C]PK11195 in a model of acute neuroinflammation (rat).[38] Moreover, competition studies demonstrated a high specific binding of [$^{11}$C]SSR180575 for TSPO.[38] However, as far as the authors are aware, no studies to date have been reported for the use of isotopically labeled SSR180575 for PET imaging in oncology. Since one goal of the present invention was to explore 3 as a potential radiopharmaceutical lead for translation into preclinical cancer imaging studies, radiofluorination was deemed to be the most effective means to achieve this goal. Though useful in the research setting, the 20.4 min half-life of $^{11}$C limits broader utility of the tracer (shipment to satellite locations, dynamic PET studies), thus making $^{18}$F (109.4 min half-life) an attractive alternative.

The present inventors initially applied microfluidic-radiolabeling approaches to elucidate stability and ascertain labeling feasibility of precursors 15 and 16. Using a commercial microfluidic module (NanoTek®) that enabled carefully controlled stoichiometry between [$^{18}$F]$^-$ and precursor at set temperatures (° C.) with controllable reaction times (μL/min flow rates), we carried out multiple, small-scale, sequential radiolabelings in a relatively short amount of time, allowing rapid optimization of labeling conditions (Table 2). The information gathered with the NanoTek® module was used to better inform the transition to the GE TRACERlab™ FX$_{F-N}$ module for larger, preclinical-scale productions. Using cyclotron-generated $^{18}$F$^-$ and K$^+$-K$_{2.2.2}$/K$_2$CO$_3$ in anhydrous DMSO, a series of reaction temperatures (80-180° C.) at a transfer rate of 40 μL/min was investigated, with product formation monitored by radio-TLC for % $^{18}$F-incorporation (Table 2). For the chloro precursor (15), product formation was observed at 180° C. (1.41%) at a transfer rate of 40 μL/min. Maintaining a reaction temperature of 180° C. and decreasing the transfer rate to 14 μL/min gave modest incorporation (5.2%, Table 2, entry 3). Similar results were obtained using precursor 16 (Table 2, entry 6). Despite modest yields, the data generated from these experiments also highlighted the thermal stability (up to 180° C.) of both 15 and 16, verified by HPLC of crude reaction mixtures. Bromo-precursor 16 demonstrated particularly optimal chromatographic resolution from the final product ([$^{18}$F]-14). These observations provided a confident basis to pursue the radiolabeling reaction in a sealed system at 180° C. for a longer period of time.

TABLE 2

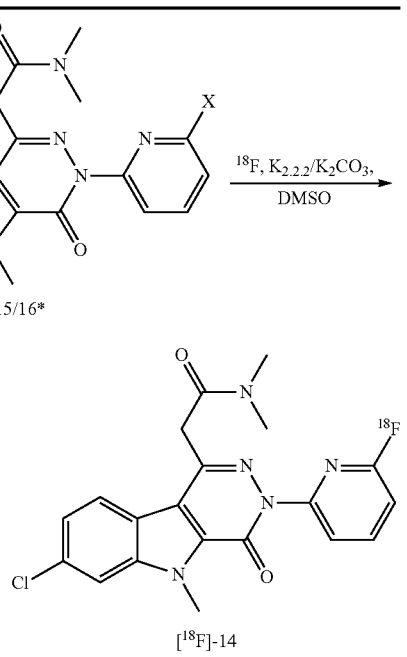

| Run | X | Temp (° C.) | Transfer Rate (μl) | RCY (%) |
|---|---|---|---|---|
| 1 | Cl | 140 | 40 | 0 |
| 2 | Cl | 160 | 40 | 0 |
| 3 | Cl | 180 | 14 | 5.2 |
| 4 | Br | 140 | 40 | 0 |
| 5 | Br | 160 | 40 | 1 |
| 6 | Br | 180 | 60 | 7 |

*Precursors 15 & 16 stable up to 180° C.

Adaptation of these reaction conditions to large-scale box productions enabled preclinical production of [$^{18}$F]-14 in the GE TRACERlab™ FX$_{F-N}$ module with labeling conditions of 170° C. for 15 min. A lowering of the reaction temperature from 180 to 170° C. was deemed necessary due to the limitations of heating reliability at such an extreme temperature using the TRACERlab™ platform. Purification of [$^{18}$F]-14 was carried out with preparative HPLC in 45% ethanol and 55% water. The retention time of [$^{18}$F]-14 was 23-28 min according to gamma detection and corresponded to the UV retention time of nonradioactive 14. Radiochemical purity was consistently greater than 99% (n=9), with decay-corrected yields ranging from 9.3-19.3% and specific activities as high as 5559 Ci/mmol (206 TBq/mmol) (n=9). However, the apparent specific activity was diminished using 42.5% ethanol and 57.5% water, despite the longer retention time.

Imaging Studies

Uptake Characteristics of [$^{18}$F]-14 in C6 Glioma. The in vivo performance of [$^{18}$F]-14 was evaluated in glioma-bearing (C6), male Wistar rats using microPET imaging, with a typical study shown in FIG. 1. MRI (T$_2$-weighted) was used to localize tumors and for registration of anatomical features with PET (FIG. 1A).[11,12,18] Dynamic PET imaging with [$^{18}$F]-14 illustrated that the majority of tracer accumulation in the brain was localized to the tumor, with modest accumulation that exceeded plasma in contralateral, non-tumor brain (FIGS. 1B & 1C). The tumor-selective characteristics of [$^{18}$F]-14 afforded excellent imaging contrast between tumor and contralateral tissue. FIG. 1G illustrates time—activity curves (TACs) typical of representative studies for tumor (blue), normal brain (green), and plasma (red) over a 90-min dynamic acquisition. After an initial spike in radioactivity consistent with tracer injection and rapid distribution, [$^{18}$F]-14 quickly cleared the plasma (red). We found that [$^{18}$F]-14 accumulation in the tumor (blue), relative to normal brain (green), reached a tumor-to-normal brain ratio greater than 10:1. Preliminary radio-TLC analysis of plasma samples (2, 12, 30, 60 min) taken during the scan (n=2) suggested minimal tracer metabolism over the 60 minutes (% parent at 60 min>90%).

Histological Correlation. To validate the PET, imaging-matched brains were processed for post-mortem staining and immunohistochemistry for TSPO. Ex vivo histological analysis correlated well with PET imaging data, with close agreement between tumor tissue (H&E, FIG. 1E), elevated TSPO expression (immunohistochemistry, FIG. 1F), and tumor accumulation of [$^{18}$F]-14 (FIG. 1D).

Specific Binding of [$^{18}$F]-14 in Rats. To evaluate the in vivo TSPO specificity of [$^{18}$F]-14, the present inventors performed displacement studies in C6-bearing rats using the non-radioactive analog (14). As shown in the TAC in FIG. 1H, during the dynamic PET study, a bolus (IV) infusion of nonradioactive 14 (10 mg/kg) was administered approximately 30 minutes after injection of [$^{18}$F]-14. Summation of the first 30 minutes of the PET scan prior to injection of cold 14 (0-30 min) demonstrated typical accumulation characteristics of [$^{18}$F]-14. However, summation of the final 30 minutes of the PET scan (30-60 min) demonstrated significant displacement of [$^{18}$F]-14 from tumor tissue (blue). TAC analysis demonstrated that after injection of 14, tumor binding was reduced to approximately 40% of the peak tumor uptake. During tumor displacement, the present inventors observed a minor influx of tracer into normal brain (green). The displaced [$^{18}$F]-14 then rapidly cleared the normal brain and entered the plasma, subsequently elevating plasma (red) radioactivity. These studies suggest a level of displaceable binding indicative of a high degree of specific binding and reversibility of [$^{18}$F]-14 to TSPO in tumor tissue.

In summary, an embodiment of the present invention is the shortest published synthesis of the pyridazinoindole TSPO ligand SSR180575 (3) to date. Initial SAR exploration at the N3 position of 3 provided a series of analogs of comparable potency, including (14) which could be adapted into a potential PET imaging tracer ([$^{18}$F]-14). Subsequent preclinical studies illuminated embodiments of the present invention as promising, novel TSPO PET ligands for imaging glioma. For example, compared to previous TSPO PET ligands in oncology, the first generation ligand [$^{11}$C]PK11195[39] and the second generation ligands [$^{18}$F]PBR06,[19] [$^{18}$F]DPA-714,[12] and [$^{18}$F]VUIIS1008,[13,21] [$^{18}$F]-14 has demonstrated improved binding affinity and in vivo imaging characteristics. These advantages, in addition to the in vivo stability and high signal-to-noise achieved between tumor and surrounding normal brain, show embodiments of the present invention as effective PET ligands for detection of TSPO-expressing tumors in the brain and neuroinflammation.

Supporting Information/Additional Experimental Information for this Example General Information. All commercially available reagents were used without further purification. Microwave reactions were carried out with a Biotage Initiator™ Sixty microwave system (Uppsala, Sweden), Reaction residues were purified using a CombiFlash purification system (TELEDYNE ISCO) with silica cartridges. $^1$H- and $^{13}$C-NMR spectra were recorded on a Bruker 400 MHz spectrometer in the Vanderbilt Small-Molecule NMR Facility. Chemical shifts are reported in ppm using the residual of chloroform as the internal standard (7.26 ppm for $^1$H and 77.00 ppm for $^{13}$C, respectively). The following abbreviations are used: s=singlet, d=doublet, t=triplet, q=quartet and m=multiplet. High-resolution mass spectra were obtained using a Micromass (Waters) Q-Tof API-US calibrated and verified with sodium iodide. The samples were diluted with a 50:50 0.1% Formic Acid (in Milli-Q): Acetonitrile solution, and directly infused using Leucine-Enkephalin (M+H=556.2771) as a lockmass. Scan range was from 100-1000 Da, and the scan time was one second per scan.

Synthetic and Analytic Data

Ethyl 6-chloro-1-methyl-1H-indole-2-carboxylate (5)

To a stirred solution of ethyl 6-chloroindole-2-carboxylate (2.51 g, 11.22 mmol) in dry DMF (50 mL) was added sodium hydride (539 mg, 60% wt dispersion in oil, 13.47 mmol) and the resulting suspension was stirred at room temperature for 30 min. Methyl iodide (1.05 mL, 16.03 mmol) was added and the reaction mixture was stirred at room temperature overnight. The reaction was quenched by slow addition of water (15 mL) and partitioned between ethyl acetate (75 mL) and water (75 mL). The organic layer was washed with water (3×75 mL), brine (75 mL), dried (MgSO$_4$), filtered and concentrated under vacuum. The crude product was purified by flash chromatography on silica gel (Isco 80 g) eluting with 0 to 5% ethyl acetate/hexanes to give the product 5 as a white solid (2.26 g, 85%). $^1$H-NMR (400 MHz, CDCl$_3$) δ7.58 (d, J=8.5 Hz, 1H), 7.38 (s, 1H), 7.11 (dd, J=8.5 and 1.8 Hz, 1H), 4.38 (q, J=7.1 Hz, 2H), 4.04 (s, 3H), 1.42 (t, J=7.1 Hz, 3H). $^{13}$C-NMR (100 MHz, CDCl$_3$) δ 161.9, 139.9, 131.0, 128.8, 124.3, 123.4, 121.5, 110.2, 110.1, 60.7, 31.7, 14.3. HRMS calcd for C$_{12}$H$_{13}$O$_2$Cl m/z=238.0635, found 238.0634.

Ethyl 6-chloro-3-(3-methoxy-3-oxopropanoyl)-1-methyl-1H-indole-2-carboxylate (6)

Methyl 3-chloro-3-oxopropionate (679 μL, 6.33 mmoL) was added dropwise to a stirred solution of titanium (IV) chloride (694 μL, 6.33 mmol) in 1,2-dichloroethane (8.4 mL) at room temperature and the resulting solution was stirred for 40 min. A solution of ethyl 6-chloro-1-methyl-1H-indole-2-carboxylate (500 mg, 2.11 mmol) in 1,2-dichloroethane (2.5 mL) was added dropwise and the reaction mixture was heated at 40° C. for 15 h. The reaction was quenched by pouring into ice water and extracted with methylene chloride (3×50 mL). The organic extracts were combined, washed with brine, dried (MgSO$_4$), filtered and concentrated under vacuum. The crude product was purified by flash chromatography on silica gel (Isco 24 g) eluting with 0 to 20% ethyl acetate/hexanes to give the product 6 as a tan solid (328 mg, 46%). $^1$H-NMR (400 MHz, CDCl$_3$) δ 7.99 (d, J=8.7 Hz, 1H), 7.38 (d, J=1.7 Hz, 1H), 7.26 (dd, J=8.7 Hz, 1.8 Hz, 1H), 4.50 (q, J=7.2 Hz, 2H), 3.97 (s, 3H), 3.88 (s, 3H), 3.72 (s, 3H), 1.45 (t, J=7.1 Hz, 3H). $^{13}$C-NMR (100 MHz, CDCl$_3$) δ 189.4, 167.8, 161.8, 137.6, 132.7, 131.4, 124.1, 123.6, 123.4, 118.3, 110.3, 62.7, 52.3, 49.0, 32.0, 14.0. HRMS calcd for C$_{16}$H$_{17}$NO$_5$Cl m/z=338.0795, found 338.0795.

2-(7-Chloro-5-methyl-4-oxo-3-phenyl-4,5-dihydro-3H-pyridazino[4,5-b]indol-1-yl)-N,N-dimethylacetamide (7)

A 20-mL microwave vial was charged with ethyl 6-chloro-3-(3-methoxy-3-oxopropanoyl)-1-methyl-1H-indole-2-carboxylate (80 mg, 0.237 mmol) in toluene (2.4 mL) followed by a solution of dimethylamine in THF (2.37 mL, 2.0 M in THF, 4.74 mmol) and DMAP (3 mg, 0.0246 mmol) and stirrer bar. The vial was capped and heated at 110° C. for 15 h, cooled to room temperature and concentrated under vacuum. The crude product was purified by flash chromatography on silica gel (Isco 12 g) eluting with 0 to 70% ethyl acetate/hexanes to give the product 7 as a tan solid (64 mg, 77%). Keto-tautomer: $^1$H-NMR (400 MHz, CDCl$_3$) δ 8.01 (d, J=8.6 Hz, 1H), 7.36 (s, 1H), 7.26 (d, J=8.0 Hz, 1H), 4.49 (q, J=7.1 Hz, 2H), 4.10 (s, 2H), 3.85 (s, 3H), 3.04 (s, 3H), 2.97 (s, 3H), 1.44 (t, J=7.2 Hz, 3H). Enol-tautomer: δ 7.75 (d, J=8.5 Hz, 0.5H), 7.36 (s, 0.5H), 7.16 (d, J=8.2 Hz, 0.5H), 5.56 (br s, 0.5H), 4.39 (q, J=7.0 Hz, 1H), 3.91 (s, 1.5H), 3.05 (s, 3H), 1.37 (t, J=7.1 Hz, 1.5H). $^{13}$C-NMR (100 MHz, CDCl$_3$) keto-tautomer: δ 190.8, 167.0, 161.9, 137.5, 133.0, 131.1, 124.0, 123.4, 118.3, 110.2, 62.6, 49.0, 35.4, 32.0, 14.0. Enol tautomer: δ 172.0, 167.3, 162.0, 137.9, 130.9, 128.7, 123.5, 122.3, 116.4, 110.2, 89.1, 61.6, 37.9, 37.9, 31.7, 13.9. HRMS calcd for C$_{17}$H$_{20}$N$_2$O$_4$Cl m/z=351.1112, found 351.1110.

2-(7-Chloro-5-methyl-4-oxo-3-phenyl-4,5-dihydro-3H-pyridazino[4,5-b]indol-1-yl)-N,N-dimethylacetamide (3)

A 5-mL microwave vial was charged with 2-(7-chloro-5-methyl-4-oxo-3-phenyl-4,5-dihydro-3H-pyridazino[4,5-b]indol-1-yl)-N,N-dimethylacetamide (37 mg, 0.106 mmol) in absolute ethanol (1.0 mL) followed by phenylhydrazine (32.6 μL, 0.331 mmol) and glacial acetic acid (50 μL, 0.873 mmol). The vial was capped and heated at 85° C. for 15 h, cooled to room temperature and concentrated under vacuum. The crude product which was purified by flash chromatography on silica gel (Isco 12 g) eluting with 0 to 50% ethyl acetate/hexanes to give the product 3 as an off-white solid (14 mg, 34%). $^1$H-NMR (400 MHz, CDCl$_3$) δ 7.97 (d, J=8.6 Hz, 1H), 7.64 (t, J=7.4 Hz, 2H), 7.55 (d, J=1.7 Hz, 1H), 7.50 (t, J=7.5 Hz, 2H), 7.40 (t, J=7.4 Hz, 1H), 7.35 (dd, J=8.6 Hz, 1.8 Hz, 1H), 4.35 (s, 3H), 4.22 (s, 2H), 3.24 (s, 3H), 3.01 (s, 3H). $^{13}$C-NMR (100 MHz, CDCl$_3$) δ 168.4, 155.3, 141.6, 141.4, 140.4, 133.4, 131.3, 128.7, 127.9, 127.9, 126.2, 126.2, 123.4, 123.1, 119.0, 117.5, 110.7, 39.7, 37.7, 35.7, 31.7. FIRMS calcd for C$_{21}$H$_{20}$N$_4$O$_2$Cl m/z=395.1275, found 395.1273.

2-(7-Chloro-3-(2-fluorophenyl)-5-methyl-4-oxo-4,5-dihydro-3H-pyridazino[4,5-b]indol-1-yl)-N,N-dimethylacetamide (9)

A 5-mL microwave vial was charged with 2-(7-chloro-5-methyl-4-oxo-3-phenyl-4,5-dihydro-3H-pyridazino[4,5-b]indol-1-yl)-N,N-dimethylacetamide (30 mg, 0.106 mmol) in absolute ethanol (1.0 mL) followed by 2-fluorophenylhydrazine (32 mg, 0.331 mmol) and glacial acetic acid (50 μL, 0.873 mmol). The vial was capped and heated at 85° C. for 15 h, cooled to room temperature and concentrated under vacuum. The crude product was purified by flash chromatography on silica gel (Isco 12 g) eluting with 0 to 40% ethyl acetate/hexanes to give the product 9 as an off-white solid (12 mg, 34%). $^1$H-NMR (400 MHz, CDCl$_3$) δ 8.00 (d, J=8.6 Hz, 1H), 7.54 (d, J=1.7 Hz, 1H), 7.50 (dt, J=7.6 Hz, 1.7 Hz, 1H), 7.44 (ddt, J=7.6 Hz, 7.6 Hz, 1.7 Hz, 1H), 7.35 (dd, J=8.6 Hz, 1.7 Hz, 1H), 7.32-7.20 (m, 2H), 4.33 (s, 3H), 4.20 (s, 2H), 3.20 (s, 3H), 3.00 (s, 3H). $^{13}$C-NMR (100 MHz, CDCl$_3$) δ 168.3, 157.3 (J=251.0 Hz), 155.0, 141.3, 140.9, 133.5, 131.0, 130.3 (J=8 Hz), 129.4 (J=12 Hz), 129.1, 124.6 (J=4 Hz), 123.3 (J=24 Hz), 123.2, 123.2, 119.1, 117.6, 116.5 (J=20 Hz), 39.8, 37.7, 35.7, 31.7. HRMS calcd for C$_{21}$H$_{19}$N$_4$O$_2$ClF m/z=413.1181, found 413.1180.

2-(7-Chloro-3-(3-fluorophenyl)-5-methyl-4-oxo-4,5-dihydro-3H-pyridazino[4,5-b]indol-1-yl)-N,N-dimethylacetamide (10)

A 5 mL microwave vial was charged with 2-(7-chloro-5-methyl-4-oxo-3-phenyl-4,5-dihydro-3H-pyridazino[4,5-b]indol-1-yl)-N,N-dimethylacetamide (24 mg, 0.069 mmol) in absolute ethanol (1.0 mL) followed by 3-fluorophenylhydrazine hydrochloride (33 mg, 0.206 mmol) and glacial acetic acid (50 μL, 0.873 mmol). The vial was capped and heated at 85° C. for 15 h, cooled to room temperature and concentrated under vacuum. The crude product was purified by flash chromatography on silica gel (Isco 12 g) eluting with 0 to 40% ethyl acetate/hexanes to give the product 10 as an off-white solid (10 mg, 35%). $^1$H-NMR (400 MHz, CDCl$_3$) δ 7.93 (d, J=8.6 Hz, 1H), 7.54 (d, J=1.7 Hz, 1H), 7.49 (br t, J=8.4 Hz, 1H), 7.44 (m, 2H), 7.35 (dd, J=8.6 Hz, 1.7 Hz, 1H), 7.09 (ddt, J=8.3 Hz, 2.5 Hz, 1.1 Hz, 1H), 4.33 (s, 3H), 4.20 (s, 2H), 3.23 (s, 3H), 3.01 (s, 3H). $^{13}$C-NMR (100 MHz, CDCl$_3$) δ 168.3, 162.5 (J=245 Hz), 155.2, 142.9 (J=10 Hz), 141.5, 140.8, 133.5, 131.2, 129.7 (J=9 Hz), 123.3, 123.3, 121.8 (J=3 Hz), 119.0, 117.5, 114.7 (J=21 Hz), 113.8 (J=24 Hz), 110.8, 39.6, 37.7, 35.7, 31.8. HRMS calcd for C$_{11}$H$_{19}$N$_4$O$_2$ClF m/z=413.1181, found 413.1180.

2-(7-Chloro-3-(4-fluorophenyl)-5-methyl-4-oxo-4,5-dihydro-3H-pyridazino[4,5-b]indol-1-yl)-N,N-dimethylacetamide (12)

A 5-mL microwave vial was charged with 2-(7-chloro-5-methyl-4-oxo-3-phenyl-4,5-dihydro-3H-pyridazino[4,5-b]indol-1-yl)-N,N-dimethylacetamide (30 mg, 0.086 mmol) in absolute ethanol (1.0 mL) followed by 4-fluorophenylhydrazine hydrochloride (25.4 μL, 0.257 mmol) and glacial acetic acid (50 μL, 0.873 mmol). The vial was capped and heated at 85° C. for 15 h, cooled to room temperature and concentrated under vacuum. The crude product was purified by flash chromatography on silica gel (Isco 12 g) eluting with 0 to 40% ethyl acetate/hexanes to give the product 12 as an off-white solid (11 mg, 31%). $^1$H-NMR (400 MHz, CDCl$_3$) δ 7.93 (d, J=8.6 Hz, 1H), 7.65-7.59 (m, 2H), 7.55 (d, J=1.6 Hz, 1H), 7.36 (dd, J=8.6 Hz, 1.7 Hz, 1H), 7.18 (t, J=8.6 Hz, 2H), 4.34 (s, 3H), 4.20 (s, 2H), 3.24 (s, 3H), 3.02 (s, 3H). $^{13}$C-NMR (100 MHz, CDCl$_3$) δ 168.4, 161.8 (J=246 Hz), 155.3, 141.5, 140.6, 137.6, 133.5, 131.2, 128.0 (J=8.7 Hz), 123.2 (J=6.4 Hz), 123.2, 119.0, 117.5, 115.6 (J=22.7 Hz), 110.8, 39.6, 37.7, 35.7, 31.7. FIRMS calcd for C$_{11}$H$_{19}$N$_4$O$_2$ClF m/z=413.1183, found 413.1180.

2-(7-Chloro-5-methyl-3-(3-nitrophenyl)-4-oxo-4,5-dihydro-3H-pyridazino[4,5-b]indol-1-yl)-N,N-dimethylacetamide (11)

A 5-mL microwave vial was charged with 2-(7-chloro-5-methyl-4-oxo-3-phenyl-4,5-dihydro-3H-pyridazino[4,5-b]indol-1-yl)-N,N-dimethylacetamide (30 mg, 0.086 mmol) in absolute ethanol (1.0 mL) followed by 3-nitrophenylhydrazine hydrochloride (49 mg, 0.257 mmol) and glacial acetic acid (50 μL, 0.873 mmol). The vial was capped and heated at 85° C. for 15 h, cooled to room temperature and concentrated under vacuum. The crude product was purified by flash chromatography on silica gel (Isco 12 g) eluting with 0 to 50% ethyl acetate/hexanes to give the product 11 as a tan solid (19 mg, 50%). $^1$H-NMR (400 MHz, CDCl$_3$) δ 8.63 (t, J=2.1 Hz, 1H), 8.23 (dt, J=3.1 Hz, 0.9 Hz, 1H), 8.16 (dt, J=2.9 Hz, 0.9 Hz, 1H), 7.90 (d, J=8.6 Hz, 1H), 7.65 (t, J=8.2 Hz, 1H), 7.56 (d, J=1.7 Hz, 1H), 7.37 (dd, J=8.6 Hz, 1.7 Hz, 1H), 4.34 (s, 3H), 4.23 (s, 2H), 3.26 (s, 3H), 3.03 (s, 3H). $^{13}$C-NMR (100 MHz, CDCl$_3$) δ 168.2, 155.2, 148.3, 142.5, 141.6, 133.7, 131.7, 131.0, 129.2, 123.5, 123.2, 123.2, 122.2, 121.2, 118.9, 117.6, 110.9, 39.5, 37.7, 35.73, 31.9. HRMS calcd for C$_{11}$H$_{19}$N$_5$O$_4$Cl m/z=440.1126, found 440.1130.

2-(7-Chloro-5-methyl-4-oxo-3-(pyridin-2-yl)-4,5-dihydro-3H-pyridazino[4,5-b]indol-1-yl)-N,N-dimethylacetamide (13)

A 5-mL microwave vial was charged with 2-(7-chloro-5-methyl-4-oxo-3-phenyl-4,5-dihydro-3H-pyridazino[4,5-b]indol-1-yl)-N,N-dimethylacetamide (40 mg, 0.114 mmol) in absolute ethanol (1.0 mL) followed by 2-hydrazinopyridine (37 mg, 0.343 mmol) and glacial acetic acid (50 μL, 0.873 mmol). The vial was capped and heated at 85° C. for 15 h, cooled to room temperature and concentrated under vacuum. The crude product was purified by flash chromatography on silica gel (Isco 12 g) eluting with 0 to 10% CMA/methylene chloride [CMA=chloroform/methanol/ammonium hydroxide (80:18:2)] to give the product 13 as a tan solid (11 mg, 24%). $^1$H-NMR (400 MHz, CDCl$_3$) δ 8.69 (dd, J=4.8 Hz, 1.1 Hz, 1H), 7.95-7.84 (m, 2H), 7.67 (d, J=8.0 Hz, 1H), 7.54 (d, J=1.7 Hz, 1H), 7.39 (dd, J=7.3 Hz, 5.3 Hz, 1H), 7.37 (dd, J=8.7 Hz, 1.7 Hz, 1H), 4.33 (s, 3H), 4.23 (s, 2H), 3.22 (s, 3H), 2.99 (s, 3H). $^{13}$C-NMR (100 MHz, CDCl$_3$) δ 168.4, 155.5, 153.6, 149.3, 141.5, 141.0, 138.0, 133.4, 131.2, 123.4, 123.4, 123.2, 121.8, 119.1, 117.8, 110.8, 39.7, 37.6, 35.7, 31.8. FIRMS calcd for C$_{20}$H$_{19}$N$_5$O$_2$Cl m/z=396.1227, found 396.1226.

2-(7-Chloro-3-(6-fluoropyridin-2-yl)-5-methyl-4-oxo-4,5-dihydro-3H-pyridazino[4,5-b]indol-1-yl)-N,N-dimethylacetamide (14)

A 5-mL microwave vial was charged with 2-(7-chloro-5-methyl-4-oxo-3-phenyl-4,5-dihydro-3H-pyridazino[4,5-b]indol-1-yl)-N,N-dimethylacetamide (40 mg, 0.114 mmol) in absolute ethanol (1.0 mL) followed by (6-fluoropyridny-2-yl)-hydrazine (43 mg, 0.343 mmol) and glacial acetic acid (50 μL, 0.873 mmol). The vial was capped and heated at 85° C. for 15 h, cooled to room temperature and concentrated under vacuum. The crude product was purified by flash chromatography on silica gel (Isco 12 g) eluting with 0 to 5% CMA/methylene chloride [CMA=chloroform/methanol/ammonium hydroxide (80:18:2)] to give the product 14 as a tan solid (21 mg, 44%). $^1$H-NMR (400 MHz, CDCl$_3$) δ 7.98 (ddd, J=7.9 Hz, 7.9 Hz, 7.9 Hz, 1H), 7.92 (d, J=8.2 Hz, 1H), 7.60 (dd, J=7.6 Hz, 1.3 Hz, 1H), 7.55 (d, J=1.7 Hz, 1H), 7.36 (dd, J=8.6 Hz, 1.8 Hz, 1H), 7.02 (dd, J=8.1 Hz, 2.7 Hz, 1H), 4.33 (s, 3H), 4.23 (s, 2H), 3.24 (s, 3H), 3.00 (s, 3H). $^{13}$C-NMR (100 MHz, CDCl$_3$) δ 168.3, 162.6 (J=241 Hz), 155.4, 151.3 (J=13.2 Hz), 142.4 (J=7.5 Hz), 141.4 (J=23.9 Hz), 133.6, 130.9, 123.4, 123.4, 119.0, 118.9 (J=4.7 Hz), 117.8, 110.80, 109.3, 109.0, 39.7, 37.7, 35.7, 31.8. FIRMS calcd for C$_{20}$H$_{18}$N$_5$O$_2$ClF m/z=414.1133, found 414.1133.

2-(7-Chloro-3-(6-chloropyridin-2-yl)-5-methyl-4-oxo-4,5-dihydro-3H-pyridazino[4,5-b]indol-1-yl)-N,N-dimethylacetamide (15)

A 5 mL microwave vial was charged with 2-(7-chloro-5-methyl-4-oxo-3-phenyl-4,5-dihydro-3H-pyridazino[4,5-b]indol-1-yl)-N,N-dimethylacetamide (27 mg, 0.077 mmol) in absolute ethanol (1.0 mL) followed by 2-chloro-6-hydrazinopyridine (33 mg, 0.231 mmol) and glacial acetic acid (50 μL, 0.873 mmol). The vial was capped and heated at 85° C. for 15 h, cooled to room temperature and concentrated under vacuum. The crude product was purified by flash chromatography on silica gel (Isco 12 g) eluting with 0 to 5% CMA/methylene chloride [CMA=chloroform/methanol/ammonium hydroxide (80:18:2)] to give the product 15 as a tan solid (14 mg, 42%). $^1$H-NMR (400 MHz, CDCl$_3$) δ 7.93 (d, J=8.7 Hz, 1H), 7.85 (d, J=7.9 Hz, 1H), 7.62 (d, J=7.7 Hz, 1H), 7.55 (d, J=1.7 Hz, 1H), 7.42 (d, J=7.8 Hz, 1H), 7.36 (dd, J=8.6 Hz, 1.7 Hz, 1H), 4.33 (s, 3H), 4.23 (s, 2H), 3.24 (s, 3H), 3.00 (s, 3H). $^{13}$C-NMR (100 MHz, CDCl$_3$) δ 168.3, 155.4, 153.0, 150.5, 141.4, 141.2, 140.2, 133.6, 130.9, 124.1, 123.4, 123.4, 120.4, 119.0, 117.8, 110.8, 39.7, 37.7, 35.7, 31.8. HRMS calcd for C$_{20}$H$_{18}$N$_5$O$_2$Cl2 m/z=430.0838, found 430.0835.

2-(7-Chloro-3-(6-bromopyridin-2-yl)-5-methyl-4-oxo-4,5-dihydro-3H-pyridazino[4,5-b]indol-1-yl)-N,N-dimethylacetamide (16)

A 5-mL microwave vial was charged with 2-(7-chloro-5-methyl-4-oxo-3-phenyl-4,5-dihydro-3H-pyridazino[4,5-b]indol-1-yl)-N,N-dimethylacetamide (31 mg, 0.089 mmol) in absolute ethanol (1.0 mL) followed by 2-bromo-6-hydrazinopyridine (50 mg, 0.266 mmol) and glacial acetic acid (50 μL, 0.873 mmol). The vial was capped and heated at 85° C. for 15 h, cooled to room temperature and concentrated under vacuum. The crude product was purified by flash chromatography on silica gel (Isco 12 g) eluting with 0 to 5% CMA/methylene chloride [CMA=chloroform/methanol/ammonium hydroxide (80:18:2)] to give the product 16 as a tan solid (18 mg, 43%). $^1$H-NMR (400 MHz, CDCl$_3$) δ 7.92 (d, J=8.6 Hz, 1H), 7.74 (t, J=7.8 Hz, 1H), 7.64 (dd, J=7.8 Hz, 0.8 Hz, 1H), 7.56 (dd, J=7.8 Hz, 0.8 Hz, 1H), 7.54 (d, J=1.6 Hz, 1H), 7.35 (dd, J=8.6 Hz, 0.8 Hz, 1H), 4.32 (s, 3H), 4.22 (s, 2H), 3.24 (s, 3H), 3.00 (s, 3H). $^{13}$C-NMR (100 MHz, CDCl$_3$) δ 168.2, 155.3, 153.1, 141.4, 141.2, 140.6, 139.8, 133.6, 130.9, 127.9, 123.4, 123.4, 120.8, 119.0, 117.8, 110.8, 39.7, 37.7, 35.7, 31.8. FIRMS calcd for C$_{20}$H$_{18}$N$_5$O$_2$Cl Br m/z=474.0332, found 474.0329.

Radiosynthesis

In brief, using a commercial apparatus (TRACERlab™ FX$_{F-N}$; GE Healthcare), we dried aqueous $^{18}$F-fluoride ion (~3 Ci/111 GBq) by iterative cycles of addition and evaporation of acetonitrile, followed by complexation with K$^+$-K$_{2.2.2}$/K$_2$CO$_3$. The complex was then reacted with 2-(7-chloro-3-(6-bromopyridin-2-yl)-5-methyl-4-oxo-4,5-dihydro-3H-pyridazino[4,5-b]indol-1-yl)-N,N-dimethylacetamide (16, 4.0-4.5 mg) at 170° C. for 15 min in anhydrous dimethyl sulfoxide (0.6 mL). [$^{18}$F]-14 was purified using reversed-phase, high-performance liquid chromatography (C18, Dynamax 250×21.4 mm; Varian), eluting at 6.0 mL/min with water and ethanol (45/55, v/v). [$^{18}$F]-14 was collected directly into 140 mL of water (deionized), passed through a C-18 Sep-Pak (Waters) followed by sequential elution with 200-proof ethanol (1.0 mL) and saline (9.0 mL) into a sterile vial. Table S1 provides a summary of nine separate radiosyntheses in the TRACERlab™ FX$_{F-N}$ module.

The radiotracer preparation was visually inspected for clarity, absence of color, and particulates. Specific activity of the radiotracer was calculated from four (4) individual radiolabeling processes based on HPLC chromatography. The specific radioactivity was determined as follows: a known amount of radioactive product was injected and the area of the UV absorbance peak corresponding to the radiolabelled product was determined (integration value) from the HPLC chromatogram. This value was then compared with a standard curve, generated from nonradioactive 14, relating mass to UV absorbance. The quotient of activity injected and mass gave the specific activity value.

TABLE S1

Summary of TRACERlab ™ FX$_{F-N}$ Radiosyntheses

| Run | RCY/DCY (%) | Specific Activity (Ci/mmol) |
|---|---|---|
| 1 | 9.6/19.2 | 3800 |
| 2 | 8.6/17.8 | 3345 |
| 3 | 6.7/14.9 | 2497 |
| 4 | 8.4/18.3 | 5559 |
| 5 | 4.2/9.3 | 1666 |
| 6 | 4.7/10.6 | 3135 |
| 7 | 5.6/11.9 | 1646 |
| 8 | 7.2/14.5 | 3906 |
| 9 | 9.2/19.3 | 2983 |

In Vitro TSPO-Binding Assay

Male Wistar rats were sacrificed and the heart and kidney collected and dissected. The tissues were homogenized in 20 volumes of ice-cold PBS buffer (pH 7.4) with a Brinkmann microhomogenizer (Kinematica AG, Luzern, SW). The homogenate was collected at a protein concentration of 5.0 mg/mL and stored at −80° C. C6 cells were collected and washed with PBS buffer three times, and then frozen and thawed three times in lysis buffer (5.0 mM HEPES, 0.21 M D-mannitol, 0.07 M sucrose, 2.0 mM benzamidine, 2.0 mM toluenesulfonyl fluoride, 4.0 mM MgCl$_2$, pH 7.4) to produce C6 cell lysate (0.5 mg/mL). The crude heart and kidney preparations (0.3 mL), as well as the obtained C6 cell lysate (0.3 mL), were then incubated with [$^3$H]PK11195 (final concentration 0.6 nM) (Perkin Elmer, Waltham, Mass., USA) and TSPO ligands (Table 1) ($10^{-5}$ to $10^{-12}$ M) in a total volume of 1.0 mL for 2 h at 25° C. The reaction was terminated by rapid filtration through a Brandel harvester (Gaithersburg, Md., USA) and collection onto a filter presoaked with 0.3% polyethyleneimine. Filters were then punched out into scintillation vials and bound radioactivity measured on a Beckman LS 6000 Scintillation Counter (Brea, Calif., USA). Binding affinity (Ki) was calculated with Prism GraphPad (La Jolla, Calif., USA) using: 5.7 nM as the Kd for PK11195 in glioma; 1.0 nM as the Kd for PK11195 in rat kidney; 1.4 nM as the Kd for PK11195 in rat heart. The radioligand concentration for [$^3$H]PK11195 was 6.0 nM. All experiments were performed in triplicate.

In Vitro CBR-Binding Assay

Male Wistar rats were decapitated and the cerebral cortex collected and dissected. The cerebral cortex was homogenized in 20 volumes of ice-cold PBS buffer (pH 7.4) with a Brinkmann microhomogenizer (Kinematica AG, Luzern, SW). The homogenate was collected at a protein concentration of 5.0 mg/mL and stored at −80° C. The crude cerebral cortex preparation (0.3 mL) was incubated with [$^3$H]flunitrazepam (final concentration 0.6 nM) (Perkin Elmer) and 14 ($10^{-5}$ to $10^{-7}$ M) in a total volume of 1.0 mL for 2 h at 25° C. The reaction was terminated by rapid filtration through a Brandel harvester and collection onto a filter presoaked with 0.3% polyethyleneimine. Filters were then punched out into scintillation vials and bound radioactivity measured on a Beckman LS 6000 Scintillation Counter. Binding affinity (Ki) was calculated using Prism GraphPad (La Jolla, Calif., USA) using 1.1 nM as the Kd for flunitrazepam and a radioligand concentration of 0.6 nM. All experiments were performed in triplicate.

Rat Model

All studies involving animals were conducted in compliance with federal and institutional guidelines. Two weeks before imaging, healthy male Wistar rats were stereotactically inculcated in the right hemisphere with $1.0 \times 10^5$ C6 glioma cells (American Type Tissue Collection). Prior to imaging, all rats were affixed with venous and arterial catheters.

MRI

MRI was used to localize the C6 tumors. Rats were secured prone in a radiofrequency coil (38-mm inner diameter) and placed in a 4.7-T horizontal bore imaging system (Varian Inc., Palo Alto, Calif., USA). A constant body temperature of 37° C. was maintained using heated airflow. An initial multislice gradient-echo imaging sequence (repetition time, 150 ms; echo time, 3.5 ms; matrix, 128×128; field of view, 40×40 mm$^2$; slice thickness, 2 mm) was used to acquire 7 slices in each imaging plane (axial, coronal, sagittal) for proper positioning of subsequent scans. A multislice T$_2$-weighted fast spin-echo scan with 8 echoes and 8.0-ms echo spacing (effective echo time, 32 ms) was then collected with a repetition time of 2,000 ms; field of view of 32×32 mm$^2$; matrix of 128×128; 16 acquisitions; and 8 coronal slices of 2-mm thickness.

PET/CT

PET/CT was performed within 24 hours of MRI in rats with confirmed tumors. Tumor-bearing rats were administered [$^{18}$F]-14 via jugular catheter while in a microPET Focus 220 scanner (Siemens, Munich, Del.). Data were collected in list-mode format for 90 minutes, followed by a CT scan (microCAT II; Siemens) for attenuation correction.

The dynamic PET acquisition was divided into twelve 10-s frames for the first two minutes, three 60-second frames for the following three minutes, and seventeen 300-second frames for the duration of the scan. The raw data within each frame were then binned into three-dimensional sinograms, with a span of three and ring difference of 47. The sinograms were reconstructed into tomographic images (128×128×95) with voxel sizes of 0.095×0.095×0.08 cm$^3$, after scatter and attenuation corrections were applied, using a two-dimensional ordered-subsets expectation-maximization algorithm with 16 subsets and four iterations. Attenuation correction was accomplished by generating an attenuation map from the CT images. The CT image was first coregistered with the small animal PET image, segmented, and then projected into sinogram space with a span of 47 and ring difference of 23. Time-activity curves were generated by manually drawing 3-dimensional volumes of interest over tumor and contralateral brain using ASIPro (Siemens).

TLC Radiometabolite Analysis

Arterial blood (500 µL) was collected at 2, 12, 30, and 60 minutes following injection of 1.5 mCi of [$^{18}$F]-14. After centrifugation, the plasma was extracted with acetonitrile/water (50 µL, 7/1, v/v). The mixture was then centrifuged and the supernatant used for TLC analysis in 10% dichloromethane in methanol. Radiochromatographic data were recorded and collected using a radioisotope detector (Bioscan, Washington, D.C., USA).

Histology

Whole rat brains were harvested and fixed in 4% formalin for 48 hours, followed by paraffin embedding for immunohistochemistry. Tissue sections of 5.0-µm thicknesses were taken and stained with TSPO-specific rabbit polyclonal anti-rat/anti-mouse antibody (Novus Biologicals, LLC, Littleton, Colo., USA). Immunoreactivity was assessed using a horseradish peroxidase detection kit (Dako, Glostrup, DK). Hematoxylin and eosin staining was used to quantify cell density and tumor localization. Sections were visualized and documented using bright-field microscopy (Leica Microsystems, Inc., Buffalo Grove, Ill., USA).

This Example shows the synthesis and binding affinity of embodiments of the present invention.

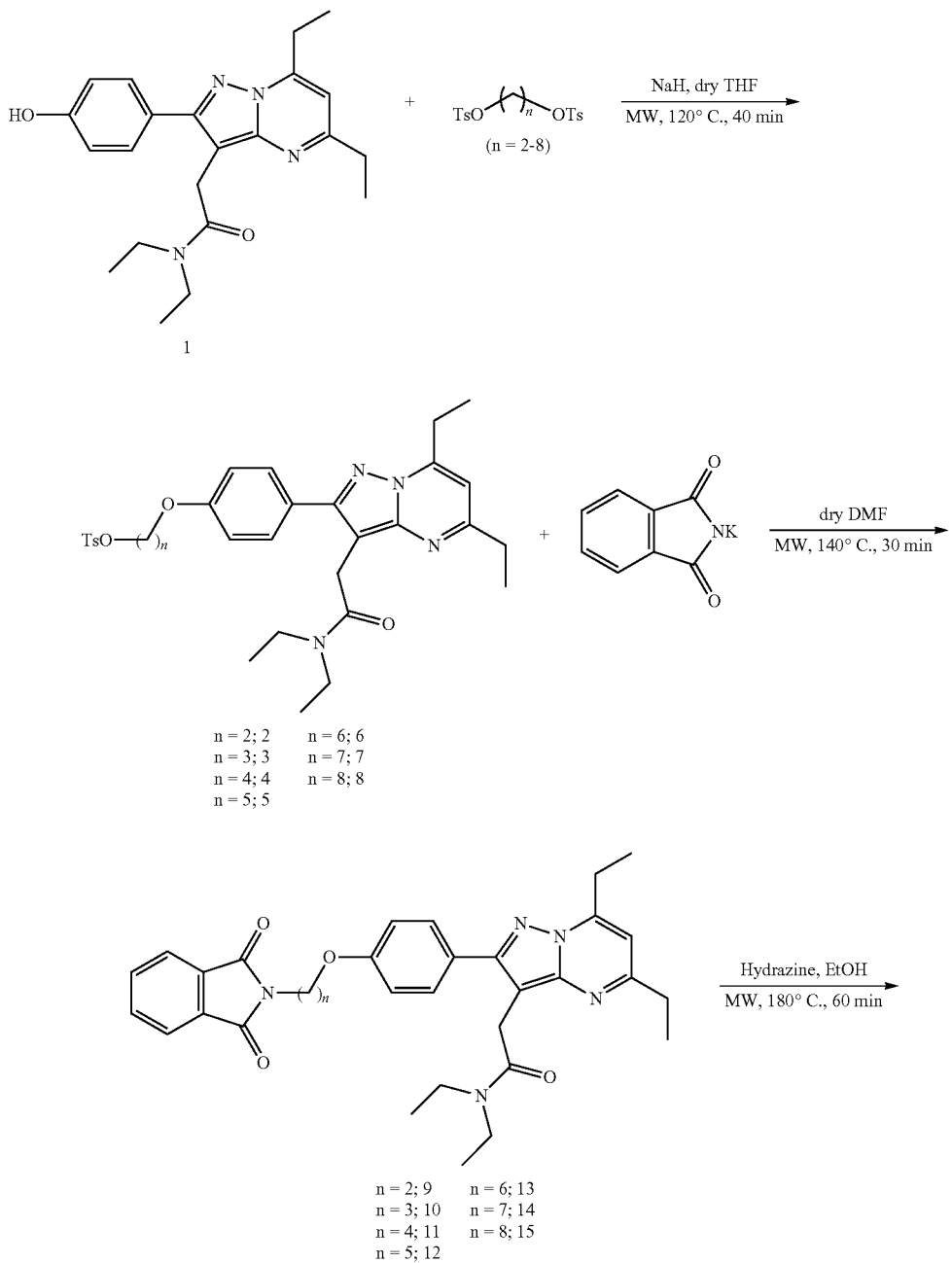

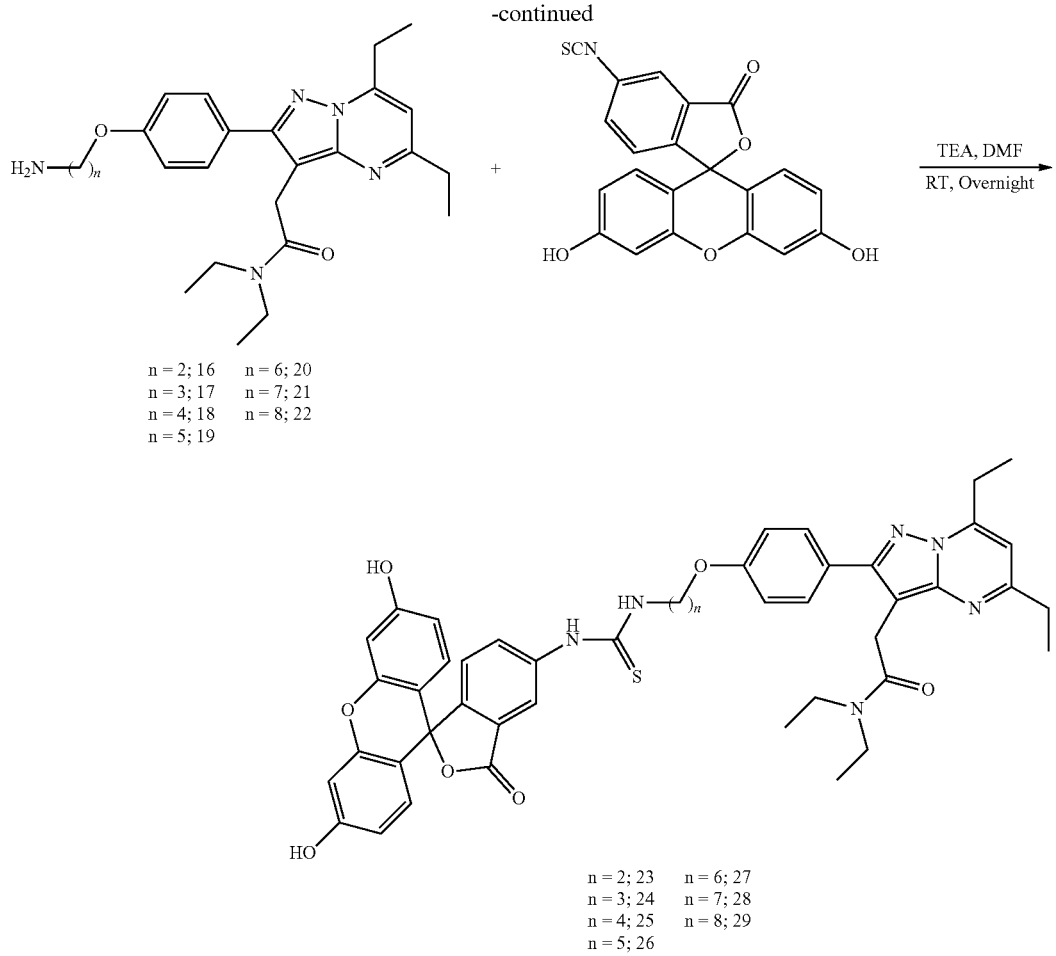

| Entry | $K_i$ (nM) |
|---|---|
| 23 (n = 2) | 13.84 ± 4.99 |
| 24 (n = 3) | 110.88 ± 25.63 |
| 25 (n = 4) | 155.47 ± 8.94 |
| 26 (n = 5) | 184.86 ± 15.39 |
| 27 (n = 6) | 11.67 ± 4.86 |
| 28 (n = 7) | 16.29 ± 5.01 |
| 29 (n = 8) | 0.31 ± 0.02 |

Binding affinity to TSPO of fluorescent probes 23-29.

Figures 2A, 2B, 2C, 2D, 2E, 2F, 2G, 2H, 2I:
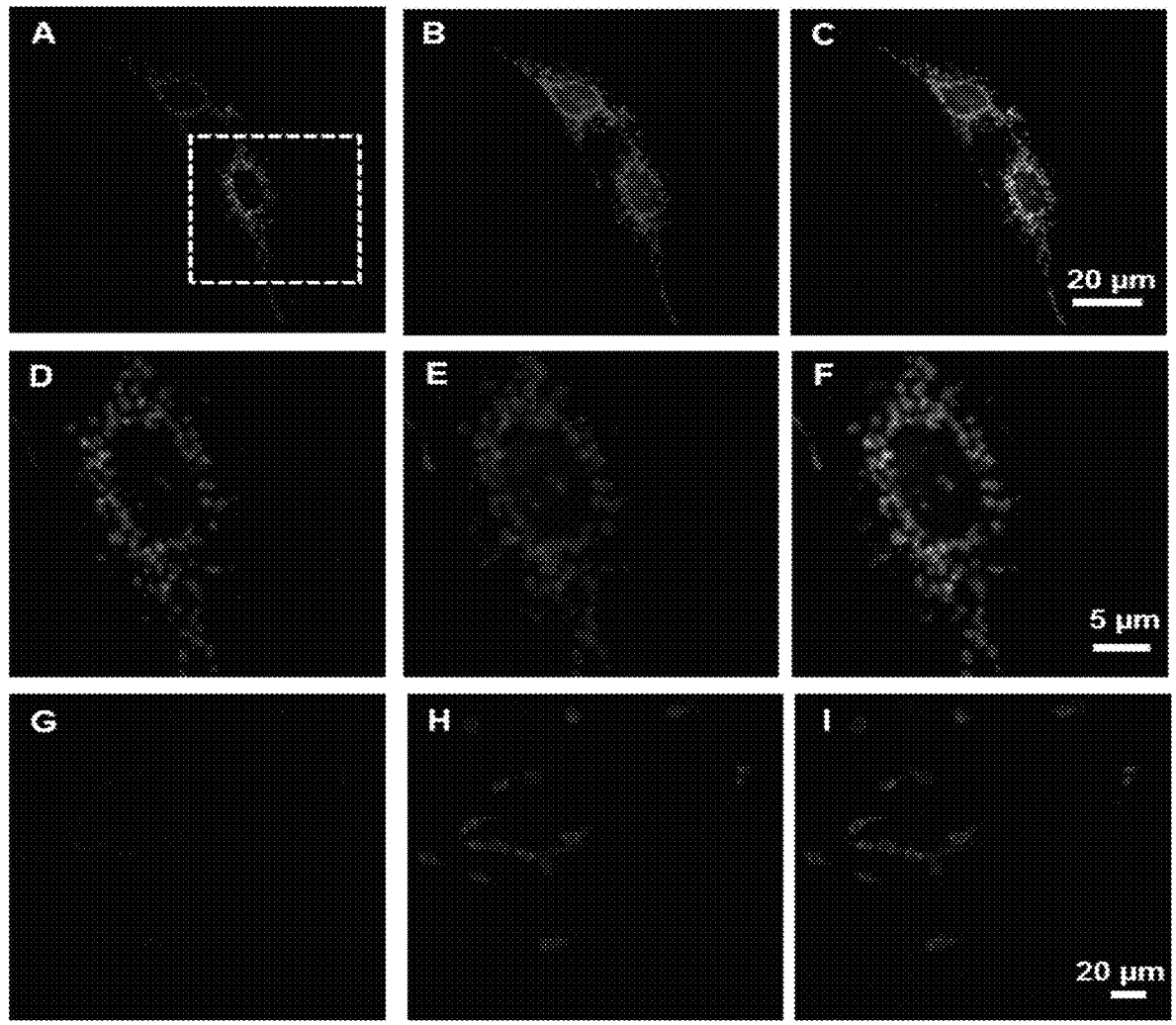
FIGS. 2A-2I shows confocal microscopy images of C6 rat glioma cells incubated with 29.

FIG. 2 is an additional example of the present invention, showing confocal microscopy images of C6 rat glioma cells incubated with an example of the present invention, particularly confocal microscopy images of C6 rat glioma cells incubated with 29. (A, D) fluorescent images of 29; (B, E) fluorescent images of Mito Tracker Red; (C, F) merged images of C8 and Mito Tracker Red. (D, E, F) fluorescent images of the chosen area in (A); (G, H, I) images of displacement experiment.

REFERENCES

The contents of all cited references (including literature references, issued patents, published patent applications) as cited throughout this application, particularly including the list below, are hereby expressly incorporated by reference. The invention and the manner and process of making and using it, are described in such full, clear, concise and exact terms as to enable any person skilled in the art to which it pertains, to make and use the same.

It is to be understood that the foregoing describes exemplary embodiments of the present invention and that modifications may be made therein without departing from the spirit or scope of the present invention as set forth in the appended claims.

(1) Dhermain, F. G.; Hau, P.; Lanfermann, H.; Jacobs, A. H.; van den Bent, M. J. *Lancet Neurol* 2010, 9, 906.
(2) Rheims, S.; Rubi, S.; Bouvard, S.; Bernard, E.; Streichenberger, N.; Guenot, M.; Le Bars, D.; Hammers, A.; Ryvlin, P. *Neuro-oncology* 2014.
(3) Jansen, N. L.; Suchorska, B.; Wenter, V.; Eigenbrod, S.; Schmid-Tannwald, C.; Zwergal, A.; Niyazi, M.; Drexler, M.; Bartenstein, P.; Schnell, O.; Tonn, J. C.; Thon, N.; Kreth, F. W.; la Fougere, C. *Journal of nuclear medicine: official publication, Society of Nuclear Medicine* 2014, 55, 198.
(4) Schwarzenberg, J.; Czernin, J.; Cloughesy, T. F.; Ellingson, B. M.; Pope, W. B.; Grogan, T.; Elashoff, D.; Geist, C.; Silverman, D. H.; Phelps, M. E.; Chen, W. *Clinical cancer research: an official journal of the American Association for Cancer Research* 2014, 20, 3550.
(5) Goldman, S.; Pirotte, B. J. *Methods Mol Biol* 2011, 727, 291.
(6) la Fougere, C.; Suchorska, B.; Bartenstein, P.; Kreth, F. W.; Tonn, J. C. *Neuro Oncol* 2011, 13, 806.
(7) Pirotte, B.; Goldman, S.; Massager, N.; David, P.; Wikler, D.; Vandesteene, A.; Salmon, I.; Brotchi, J.;

Levivier, M. *Journal of nuclear medicine: official publication, Society of Nuclear Medicine* 2004, 45, 1293.

(8) Deane, N. G.; Manning, H. C.; Foutch, A. C.; Washington, M. K.; Aronow, B. J.; Bornhop, D. J.; Coffey, R. J. *Mol Cancer Res* 2007, 5, 341.

(9) Wyatt, S. K.; Manning, H. C.; Bai, M.; Bailey, S. N.; Gallant, P.; Ma, G.; McIntosh, L.; Bornhop, D. J. *Mol Imaging Biol* 2010, 12, 349.

(10) Manning, H. C.; Goebel, T.; Thompson, R. C.; Price, R. R.; Lee, H.; Bornhop, D. J. *Bioconjug Chem* 2004, 15, 1488.

(11) Buck, J. R.; McKinley, E. T.; Hight, M. R.; Fu, A.; Tang, D.; Smith, R. A.; Tantawy, M. N.; Peterson, T. E.; Colvin, D.; Ansari, M. S.; Baldwin, R. M.; Zhao, P.; Guleryuz, S.; Manning, H. C. *Journal of nuclear medicine: official publication, Society of Nuclear Medicine* 2011, 52, 107.

(12) Tang, D.; Hight, M. R.; McKinley, E. T.; Fu, A.; Buck, J. R.; Smith, R. A.; Tantawy, M. N.; Peterson, T. E.; Colvin, D. C.; Ansari, M. S.; Nickels, M.; Manning, H. C. *Journal of nuclear medicine: official publication, Society of Nuclear Medicine* 2012, 53, 287.

(13) Tang, D.; McKinley, E. T.; Hight, M. R.; Uddin, M. I.; Harp, J. M.; Fu, A.; Nickels, M. L.; Buck, J. R.; Manning, H. C. *Journal of medicinal chemistry* 2013, 56, 3429.

(14) Papadopoulos, V.; Baraldi, M.; Guilarte, T. R.; Knudsen, T. B.; Lacapere, J. J.; Lindemann, P.; Norenberg, M. D.; Nutt, D.; Weizman, A.; Zhang, M. R.; Gavish, M. *Trends Pharmacol Sci* 2006, 27, 402.

(15) Varrone, A.; Mattsson, P.; Forsberg, A.; Takano, A.; Nag, S.; Gulyas, B.; Borg, J.; Boellaard, R.; Al-Tawil, N.; Eriksdotter, M.; Zimmermann, T.; Schultze-Mosgau, M.; Thiele, A.; Hoffmann, A.; Lammertsma, A. A.; Halldin, C. *Eur J Nucl Med Mol Imaging* 2013, 40, 921.

(16) Suridjan, I.; Rusjan, P. M.; Voineskos, A. N.; Selvanathan, T.; Setiawan, E.; Strafella, A. P.; Wilson, A. A.; Meyer, J. H.; Houle, S.; Mizrahi, R. *Neuroimage* 2013.

(17) Takano, A.; Piehl, F.; Hillert, J.; Varrone, A.; Nag, S.; Gulyas, B.; Stenkrona, P.; Villemagne, V. L.; Rowe, C. C.; Macdonell, R.; Tawil, N. A.; Kucinski, T.; Zimmermann, T.; Schultze-Mosgau, M.; Thiele, A.; Hoffmann, A.; Halldin, C. *EJNMMI research* 2013, 3, 30.

(18) Batarseh, A.; Papadopoulos, V. *Mol Cell Endocrinol* 2010.

(19) Buck, J. R.; Saleh, S.; Uddin, M. I.; Manning, H. C. *Tetrahedron letters* 2012, 53, 4161.

(20) Powell, A. E.; Vlacich, G.; Zhao, Z. Y.; McKinley, E. T.; Washington, M. K.; Manning, H. C.; Coffey, R. J. *American journal of physiology. Gastrointestinal and liver physiology* 2014, 307, G16.

(21) Tang, D.; Nickels, M. L.; Tantawy, M. N.; Buck, J. R.; Manning, H. C. *Mol Imaging Biol* 2014.

(22) Bribes, E.; Bourrie, B.; Esclangon, M.; Galiegue, S.; Vidal, H.; Casellas, P. *Eur J Pharmacol* 2002, 452, 111.

(23) Ferzaz, B.; Brault, E.; Bourliaud, G.; Robert, J. P.; Poughon, G.; Claustre, Y.; Marguet, F.; Liere, P.; Schumacher, M.; Nowicki, J. P.; Fournier, J.; Marabout, B.; Sevrin, M.; George, P.; Soubrie, P.; Benavides, J.; Scatton, B. *J Pharmacol Exp Ther* 2002, 301, 1067.

(24) Leducq, N.; Bono, F.; Sulpice, T.; Vin, V.; Janiak, P.; Fur, G. L.; O'Connor, S. E.; Herbert, J. M. *J Pharmacol Exp Ther* 2003, 306, 828.

(25) Vin, V.; Leducq, N.; Bono, F.; Herbert, J. M. *Biochemical and biophysical research communications* 2003, 310, 785.

(26) Kunduzova, O. R.; Escourrou, G.; De La Farge, F.; Salvayre, R.; Seguelas, M. H.; Leducq, N.; Bono, F.; Herbert, J. M.; Parini, A. *Journal of the American Society of Nephrology: JASN* 2004, 15, 2152.

(27) Galiegue, S.; Tinel, N.; Casellas, P. *Curr Med Chem* 2003, 10, 1563.

(28) Bribes, E.; Galiegue, S.; Bourrie, B.; Casellas, P. *Immunology Letters* 2003, 85, 13.

(29) Bribes, E.; Bourrie, B.; Casellas, P. *Immunology Letters* 2003, 88, 241.

(30) Leducq-Alet, N.; Vin, V.; Savi, P.; Bono, F. *Biochemical and biophysical research communications* 2010, 399, 475.

(31) Ferzaz, B.; Benavides, J.; Marguet, F.; Froissant, J.; Marabout, B.; Evanno, Y.; Sevrin, M.; Janiak, P.; Organization, W. I. P., Ed.; Sanofi-Synthelabo: France, 2000, p 32.

(32) Evanno, Y.; Dubois, L.; Sevrin, M.; Marguet, F.; Froissant, J.; Bartsch, R.; Gille, C.; Organization, W. I. P., Ed.; Synthelabo S. A.: France, 1999.

(33) Scarf, A. M.; Kassiou, M. *Journal of nuclear medicine: official publication, Society of Nuclear Medicine* 2011, 52, 677.

(34) Owen, D. R.; Yeo, A. J.; Gunn, R. N.; Song, K.; Wadsworth, G.; Lewis, A.; Rhodes, C.; Pulford, D. J.; Bennacef, I.; Parker, C. A.; StJean, P. L.; Cardon, L. R.; Mooser, V. E.; Matthews, P. M.; Rabiner, E. A.; Rubio, J. P. *Journal of cerebral blood flow and metabolism: official journal of the International Society of Cerebral Blood Flow and Metabolism* 2012, 32, 1.

(35) Yoder, K. K.; Nho, K.; Risacher, S. L.; Kim, S.; Shen, L.; Saykin, A. J. *Journal of nuclear medicine: official publication, Society of Nuclear Medicine* 2013, 54, 1320.

(36) Benavides, J.; Boutin, H.; Castel, M.-N.; Damont, A.; Dolle, F.; Hantraye, P.; Marguet, F.; Rooney, T.; Rivron, L.; Tavitian, B.; Thominiaux, C.; Sanofi-Aventis, Fr.; Commissariat a l'Energie Atomique C.E.A.: France, 2010, p 40.

(37) Thominiaux, C.; Damont, A.; Kuhnast, B.; Demphel, S.; Helleix, S. L.; Boisnard, S.; Rivron, L.; Chauveau, F.; Boutin, H.; Camp, N. V.; Boisgard, R.; Roy, S.; Allen, J.; Rooney, T.; Benavides, J.; Hantraye, P.; Tavitian, B.; Dolle, F. *Journal of Labelled Compounds & Radiopharmaceuticals* 2010, 53, 767.

(38) Chauveau, F.; Boutin, H.; Van Camp, N.; Thominiaux, C.; Hantraye, P.; Rivron, L.; Marguet, F.; Castel, M. N.; Rooney, T.; Benavides, J.; Dolle, F.; Tavitian, B. *Eur J Nucl Med Mol Imaging* 2011, 38, 509.

(39) Starostarubinstein, S.; Ciliax, B. J.; Penney, J. B.; Mckeever, P.; Young, A. B. *Proceedings of the National Academy of Sciences of the United States of America* 1987, 84, 891.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:
1. A compound of the following formula:
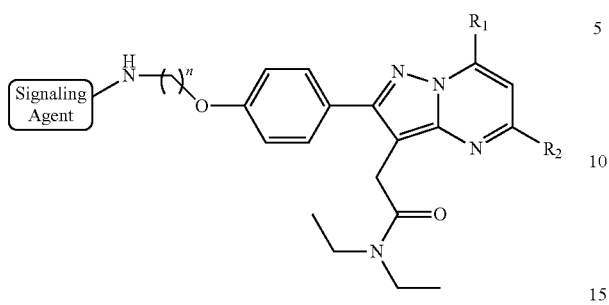
wherein $R_1$ and $R_2$ are independently ethyl; and n is 8.
2. A compound of claim 1, wherein the signaling agent is chosen from:
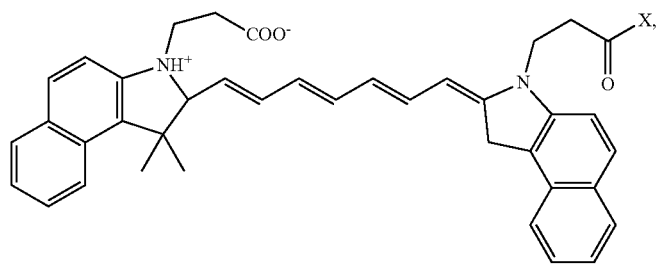
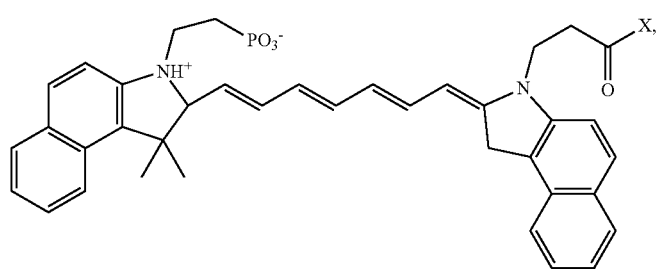
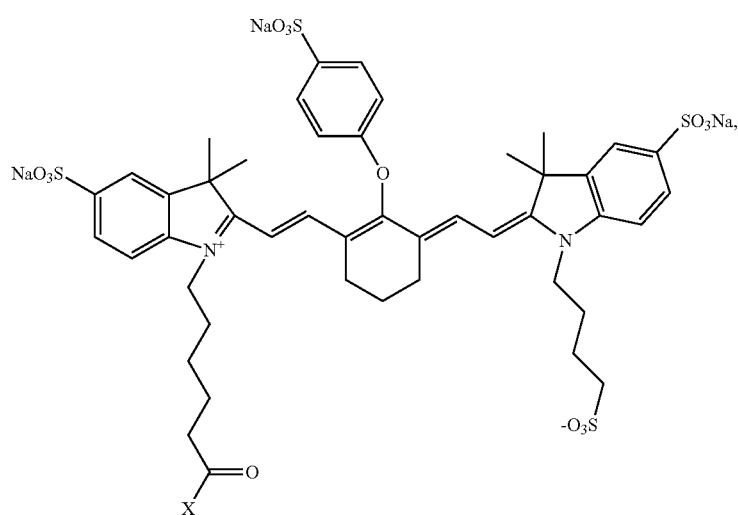

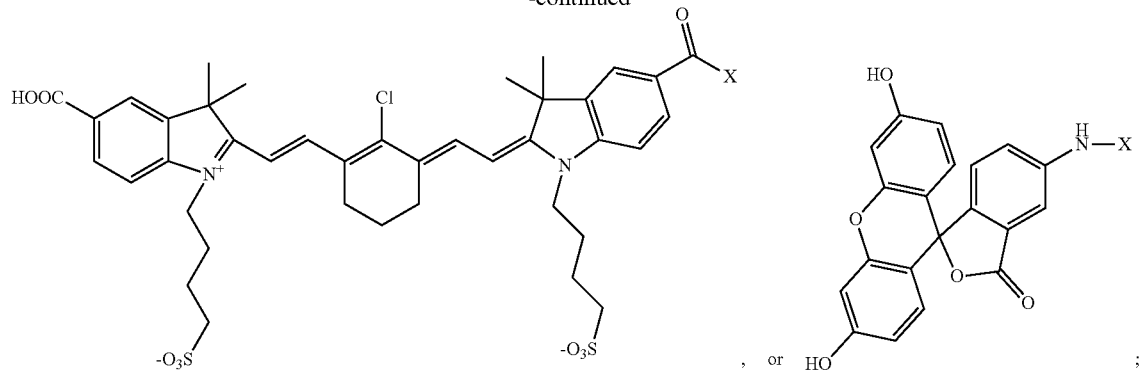

, or wherein X is the conjugation site.

3. A compound of claim 1, of the following formula:

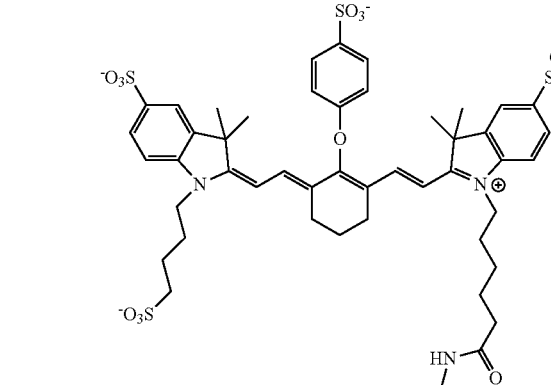

4. A method of quantifying the progression of a disease state in a subject, comprising:

(a) administering to a first sample of the subject a conjugate, the conjugate comprising a TSPO affinity ligand of the following formula:

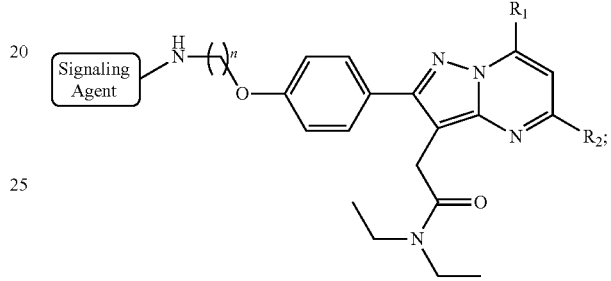

wherein $R_1$ and $R_2$ are independently ethyl, and n is 8;

(b) detecting a signal from said conjugate;

(c) after a period of time from step (b), administering to a second sample of the subject a conjugate, the conjugate comprising TSPO affinity ligand of the following formula:

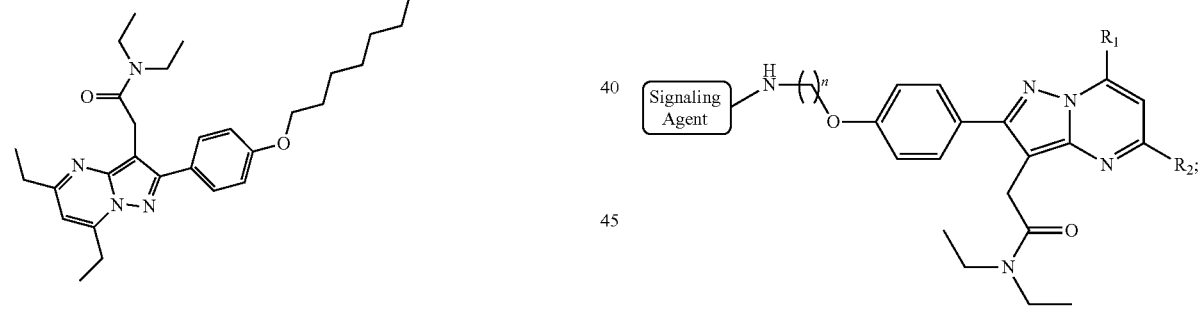

wherein $R_1$ and $R_2$ are independently ethyl, and n is 8;

(d) detecting a second signal; and (e) comparing the first signal with the second signal to determine the progress of a disease state.

5. The method of claim 4, wherein the signaling agent is selected from the following formula:

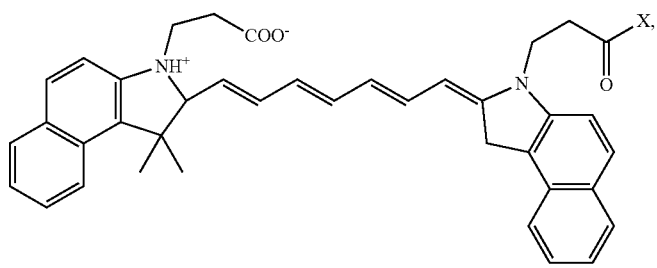

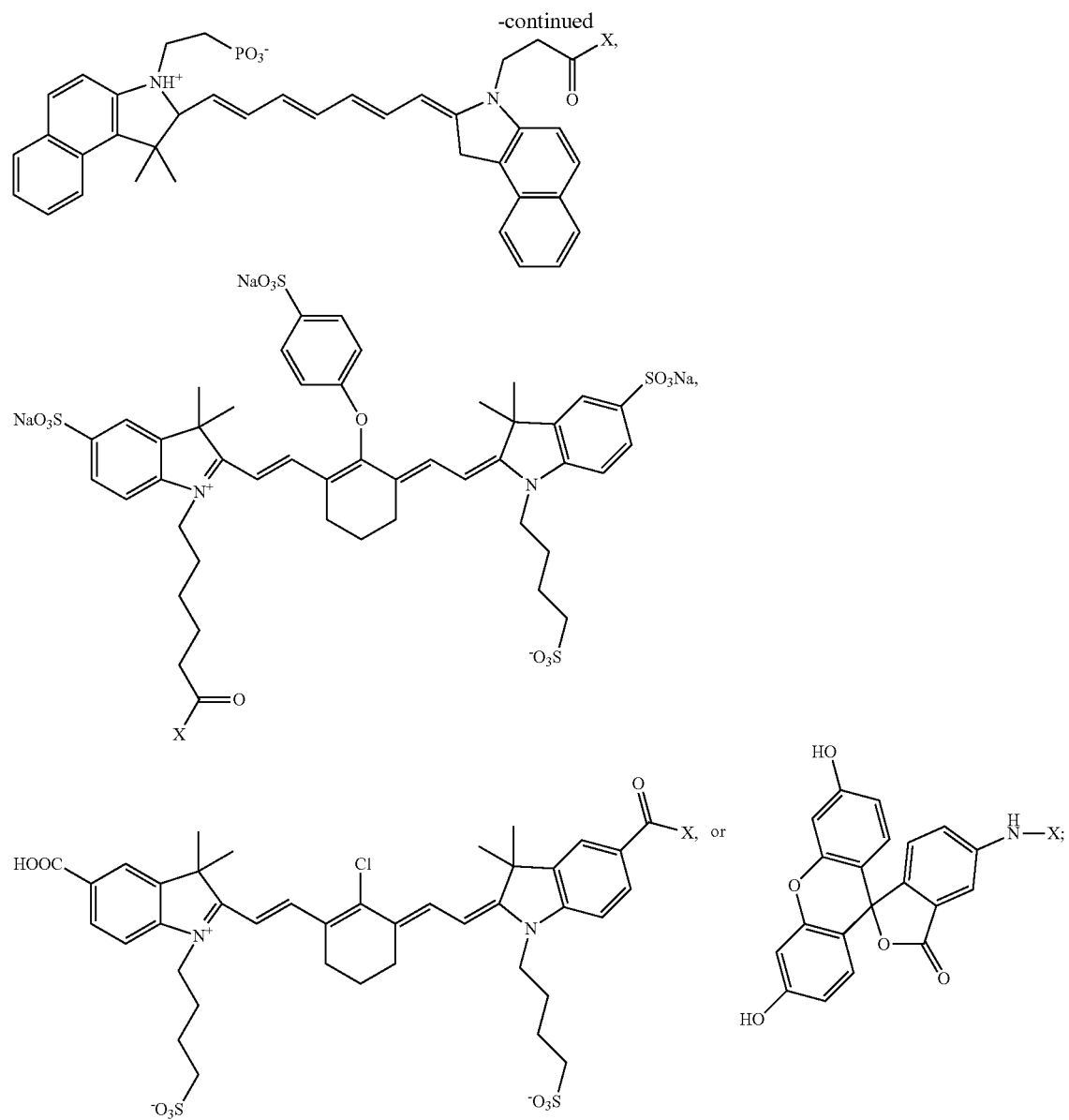
wherein X is the conjugation site.
6. The method of claim 4, where in the disease state is breast cancer, non-Hodgkin's lymphoma, colon cancer.
7. The method of claim 4, wherein the period of time between step (b) and the administering to a second sample step, includes a treatment step for said disease state.
* * * * *

UNITED STATES PATENT AND TRADEMARK OFFICE
CERTIFICATE OF CORRECTION

| | |
|---|---|
| PATENT NO. | : 11,027,027 B2 |
| APPLICATION NO. | : 15/012795 |
| DATED | : June 8, 2021 |
| INVENTOR(S) | : Manning et al. |

It is certified that error appears in the above-identified patent and that said Letters Patent is hereby corrected as shown below:

In the Specification

Replace first paragraph, which appears Column 1, Lines 6-9 with the following:
Government Support
This invention was made with government support under Grant Nos. CA095103, CA126588, CA127349, CA128323, CA163806, DK058404, and RR017858, awarded by the National Institutes of Health, awarded by U.S. Department of Energy. The government has certain rights in the invention.

Signed and Sealed this
Fifth Day of September, 2023

Katherine Kelly Vidal
*Director of the United States Patent and Trademark Office*